US010226330B2

(12) United States Patent
Spence et al.

(10) Patent No.: US 10,226,330 B2
(45) Date of Patent: Mar. 12, 2019

(54) REPLACEMENT HEART VALVE APPARATUS AND METHODS

(71) Applicant: Mitral Valve Technologies Sarl, Montreaux (CH)

(72) Inventors: Paul A. Spence, Louisville, KY (US); Landon H. Tompkins, La Grange, KY (US); Mark Chau, Aliso Viejo, CA (US); Alexander J. Siegel, Costa Mesa, CA (US)

(73) Assignee: Mitral Valve Technologies Sarl, Nyon (CH)

( * ) Notice: Subject to any disclaimer, the term of this patent is extended or adjusted under 35 U.S.C. 154(b) by 120 days.

(21) Appl. No.: 14/912,067

(22) PCT Filed: Aug. 14, 2014

(86) PCT No.: PCT/US2014/051095
§ 371 (c)(1),
(2) Date: Feb. 12, 2016

(87) PCT Pub. No.: WO2015/023862
PCT Pub. Date: Feb. 19, 2015

(65) Prior Publication Data
US 2016/0184095 A1 Jun. 30, 2016

Related U.S. Application Data

(60) Provisional application No. 61/865,657, filed on Aug. 14, 2013, provisional application No. 61/942,300, (Continued)

(51) Int. Cl.
*A61F 2/24* (2006.01)

(52) U.S. Cl.
CPC .......... *A61F 2/2409* (2013.01); *A61F 2/2412* (2013.01); *A61F 2/2418* (2013.01); (Continued)

(58) Field of Classification Search
CPC .... A61F 2/2409; A61F 2/2412; A61F 2/2418; A61F 2/2427; A61F 2/2436;
(Continued)

(56) References Cited

U.S. PATENT DOCUMENTS

| 3,564,617 A | 2/1971 | Sauvage et al. |
| 3,755,823 A | 9/1973 | Hancock |

(Continued)

FOREIGN PATENT DOCUMENTS

| CN | 1684644 A | 10/2005 |
| CN | 1714766 A | 1/2006 |

(Continued)

OTHER PUBLICATIONS

Kempfert et al., "Minimally invasive off-pump valve-in-a-ring implantation: the atrial transcatheter approach for re-operative mitral valve replacement after failed repair," European Journal of Cardiothoracic Surgery, 2009, 35:965-969.

(Continued)

*Primary Examiner* — Katrina M Stransky
(74) *Attorney, Agent, or Firm* — Thomas C. Richardson

(57) ABSTRACT

Systems and methods for replacing a heart valve. An expansible helical anchor is formed as multiple coils to support a valve prosthesis. At least one of the coils is expandable to a second, larger diameter upon application force from within the anchor. A gap is defined between adjacent coils sufficient to prevent engagement by at least one of the adjacent coils with the native heart valve. An expansible heart valve prosthesis is provided and is configured to be delivered into the anchor and expanded inside the coils into engagement. This moves the coil from the first diameter to the second diameter while securing the anchor and prosthesis together. The system further includes a seal on the expansible heart valve prosthesis configured to engage the helical anchor and (Continued)

prevent blood leakage past the heart valve prosthesis after implantation of the heart valve prosthesis in the helical anchor.

23 Claims, 28 Drawing Sheets

Related U.S. Application Data filed on Feb. 20, 2014, provisional application No. 61/943,125, filed on Feb. 21, 2014.

(52) U.S. Cl.
CPC .......... *A61F 2/2427* (2013.01); *A61F 2/2436* (2013.01); *A61F 2210/0014* (2013.01); *A61F 2230/0069* (2013.01); *A61F 2230/0091* (2013.01); *A61F 2250/006* (2013.01)

(58) Field of Classification Search
CPC ...... A61F 2230/0069; A61F 2230/0091; A61F 2250/006
See application file for complete search history.

(56) References Cited

U.S. PATENT DOCUMENTS

| | | |
|---|---|---|
| 4,035,849 A | 7/1977 | Angell et al. |
| 4,490,859 A | 1/1985 | Black et al. |
| 4,512,338 A | 4/1985 | Balko et al. |
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,403,305 A | 4/1995 | Sauter et al. |
| 5,411,552 A | 5/1995 | Andersen et al. |
| 5,443,500 A | 8/1995 | Sigwart |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,925,063 A | 7/1999 | Khosravi |
| 5,957,949 A | 9/1999 | Leonhardt et al. |
| 6,027,525 A | 2/2000 | Suh et al. |
| 6,120,534 A | 9/2000 | Ruiz |
| 6,168,614 B1 | 1/2001 | Andersen et al. |
| 6,221,091 B1 | 4/2001 | Khosravi |
| 6,235,042 B1 | 5/2001 | Katzman |
| 6,245,102 B1 | 6/2001 | Jayaraman |
| 6,302,906 B1 | 10/2001 | Goicoechea et al. |
| 6,306,141 B1 | 10/2001 | Jervis |
| 6,406,492 B1 | 6/2002 | Lytle |
| 6,409,758 B2 | 6/2002 | Stobie et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,582,462 B1 | 6/2003 | Andersen et al. |
| 6,625,578 B2 | 9/2003 | Spaur et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,971,998 B2 | 12/2005 | Rosenman et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,404,824 B1 | 7/2008 | Webler et al. |
| 7,431,726 B2 | 10/2008 | Spence et al. |
| 7,445,632 B2 | 11/2008 | McGuckin, Jr. et al. |
| 7,462,191 B2 | 12/2008 | Spenser et al. |
| 7,510,575 B2 | 3/2009 | Spenser et al. |
| 7,527,646 B2 | 5/2009 | Rahdert et al. |
| 7,585,321 B2 | 9/2009 | Cribier |
| 7,618,446 B2 | 11/2009 | Andersen et al. |
| 7,618,449 B2 | 11/2009 | Tremulis et al. |
| 7,655,034 B2 | 2/2010 | Mitchell et al. |
| 7,708,775 B2 | 5/2010 | Rowe et al. |
| 7,737,060 B2 | 6/2010 | Strickler et al. |
| 7,758,639 B2 | 7/2010 | Mathis |
| 7,780,726 B2 | 8/2010 | Seguin |
| 7,785,366 B2 | 8/2010 | Maurer et al. |
| 7,942,927 B2 | 5/2011 | Kaye et al. |
| 7,951,195 B2 | 5/2011 | Antonsson et al. |
| 7,955,385 B2 | 6/2011 | Crittenden |
| 7,959,672 B2 | 6/2011 | Salahieh et al. |
| 7,993,394 B2 | 8/2011 | Hariton et al. |
| 8,016,882 B2 | 9/2011 | Macoviak et al. |
| 8,029,556 B2 | 10/2011 | Rowe |
| 8,052,750 B2 | 11/2011 | Tuval et al. |
| 8,092,520 B2 | 1/2012 | Quadri |
| 8,128,691 B2 | 3/2012 | Keranen |
| 8,167,932 B2 | 5/2012 | Bourang et al. |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,734,507 B2 | 5/2014 | Keranen |
| 8,795,352 B2 | 8/2014 | O'Beirne et al. |
| 8,986,373 B2 | 3/2015 | Chau et al. |
| 9,078,747 B2 | 7/2015 | Conklin |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 2002/0026094 A1 | 2/2002 | Roth |
| 2002/0032481 A1 | 3/2002 | Gabbay |
| 2002/0045936 A1 | 4/2002 | Moe |
| 2002/0107535 A1 | 8/2002 | Wei et al. |
| 2002/0138135 A1 | 9/2002 | Duerig et al. |

(56) References Cited

U.S. PATENT DOCUMENTS

| | | | |
|---|---|---|---|
| 2002/0173841 A1* | 11/2002 | Ortiz | A61F 2/2409 623/2.11 |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0167089 A1 | 9/2003 | Lane | |
| 2003/0212454 A1 | 11/2003 | Scott et al. | |
| 2003/0225420 A1 | 12/2003 | Wardle | |
| 2004/0111006 A1 | 6/2004 | Alferness et al. | |
| 2004/0167620 A1 | 8/2004 | Ortiz et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0096736 A1 | 5/2005 | Osse et al. | |
| 2005/0119682 A1 | 6/2005 | Nguyen et al. | |
| 2005/0119735 A1 | 6/2005 | Spence et al. | |
| 2005/0137691 A1 | 6/2005 | Salahieh et al. | |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0025857 A1 | 2/2006 | Bergheim et al. | |
| 2006/0058872 A1 | 3/2006 | Salahieh et al. | |
| 2006/0149350 A1 | 7/2006 | Patel et al. | |
| 2006/0195185 A1 | 8/2006 | Lane et al. | |
| 2006/0265056 A1 | 11/2006 | Nguyen et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0185572 A1 | 8/2007 | Solem et al. | |
| 2007/0203503 A1 | 8/2007 | Salahieh et al. | |
| 2007/0203575 A1 | 8/2007 | Forster et al. | |
| 2007/0213813 A1 | 9/2007 | Von Segesser et al. | |
| 2007/0232898 A1 | 10/2007 | Huynh et al. | |
| 2007/0244553 A1 | 10/2007 | Rafiee et al. | |
| 2007/0265700 A1 | 11/2007 | Eliasen et al. | |
| 2007/0293808 A1 | 12/2007 | Williams et al. | |
| 2008/0004697 A1 | 1/2008 | Lichtenstein et al. | |
| 2008/0033542 A1 | 2/2008 | Antonsson et al. | |
| 2008/0114442 A1 | 5/2008 | Mitchell et al. | |
| 2008/0125853 A1 | 5/2008 | Bailey et al. | |
| 2008/0208330 A1 | 8/2008 | Keranen | |
| 2008/0228265 A1 | 9/2008 | Spence et al. | |
| 2008/0243245 A1 | 10/2008 | Thambar et al. | |
| 2008/0275503 A1 | 11/2008 | Spence et al. | |
| 2009/0005863 A1 | 1/2009 | Goetz et al. | |
| 2009/0088836 A1* | 4/2009 | Bishop | A61F 2/2418 623/2.1 |
| 2009/0099653 A1 | 4/2009 | Suri et al. | |
| 2009/0157175 A1 | 6/2009 | Benichou | |
| 2009/0177278 A1 | 7/2009 | Spence | |
| 2009/0234318 A1 | 9/2009 | Loulmet et al. | |
| 2009/0259307 A1 | 10/2009 | Gross et al. | |
| 2009/0276038 A1 | 11/2009 | Tremulis et al. | |
| 2009/0276040 A1 | 11/2009 | Rowe et al. | |
| 2009/0281619 A1 | 11/2009 | Le et al. | |
| 2009/0299471 A1 | 12/2009 | Keranen | |
| 2009/0319037 A1 | 12/2009 | Rowe et al. | |
| 2010/0049313 A1 | 2/2010 | Alon et al. | |
| 2010/0076549 A1 | 3/2010 | Keidar et al. | |
| 2010/0145440 A1* | 6/2010 | Keranen | A61F 2/2445 623/2.37 |
| 2010/0152839 A1 | 6/2010 | Shandas et al. | |
| 2010/0161047 A1 | 6/2010 | Cabiri | |
| 2010/0168844 A1 | 7/2010 | Toomes et al. | |
| 2010/0198347 A1 | 8/2010 | Zakay et al. | |
| 2010/0217382 A1 | 8/2010 | Chau et al. | |
| 2010/0217385 A1 | 8/2010 | Thompson et al. | |
| 2010/0312333 A1 | 12/2010 | Navia et al. | |
| 2010/0318183 A1 | 12/2010 | Keranen | |
| 2010/0318184 A1 | 12/2010 | Spence | |
| 2010/0331971 A1* | 12/2010 | Keranen | A61F 2/2445 623/2.11 |
| 2010/0331973 A1 | 12/2010 | Keranen | |
| 2011/0015729 A1 | 1/2011 | Jimenez et al. | |
| 2011/0098802 A1 | 4/2011 | Braido et al. | |
| 2011/0106247 A1 | 5/2011 | Miller et al. | |
| 2011/0137397 A1 | 6/2011 | Chau et al. | |
| 2011/0178597 A9 | 7/2011 | Navia et al. | |
| 2011/0196480 A1 | 8/2011 | Cartledge | |
| 2011/0208297 A1 | 8/2011 | Tuval et al. | |
| 2011/0208298 A1 | 8/2011 | Tuval et al. | |
| 2011/0218621 A1 | 9/2011 | Antonsson et al. | |
| 2011/0224785 A1 | 9/2011 | Hacohen | |
| 2011/0245911 A1 | 10/2011 | Quill et al. | |
| 2011/0288634 A1 | 11/2011 | Tuval et al. | |
| 2011/0295361 A1 | 12/2011 | Claiborne, III et al. | |
| 2011/0319989 A1 | 12/2011 | Lane et al. | |
| 2011/0319990 A1 | 12/2011 | Macoviak et al. | |
| 2012/0016464 A1 | 1/2012 | Seguin | |
| 2012/0022633 A1 | 1/2012 | Olson et al. | |
| 2012/0053680 A1 | 3/2012 | Bolling et al. | |
| 2012/0059458 A1 | 3/2012 | Buchbinder et al. | |
| 2012/0123529 A1 | 5/2012 | Levi et al. | |
| 2012/0150287 A1 | 6/2012 | Forster et al. | |
| 2012/0259409 A1 | 10/2012 | Nguyen et al. | |
| 2012/0283820 A1 | 11/2012 | Tseng et al. | |
| 2012/0310328 A1 | 12/2012 | Olson et al. | |
| 2012/0316643 A1 | 12/2012 | Keranen | |
| 2013/0006352 A1 | 1/2013 | Yaron | |
| 2013/0023985 A1 | 1/2013 | Khairkhahan et al. | |
| 2013/0114214 A1 | 5/2013 | Takeguchi et al. | |
| 2013/0190857 A1 | 7/2013 | Mitra et al. | |
| 2013/0274873 A1 | 10/2013 | Delaloye et al. | |
| 2013/0310917 A1 | 11/2013 | Richter et al. | |
| 2013/0310928 A1 | 11/2013 | Morriss et al. | |
| 2013/0317598 A1 | 11/2013 | Rowe et al. | |
| 2013/0325114 A1 | 12/2013 | McLean et al. | |
| 2013/0331929 A1 | 12/2013 | Mitra et al. | |
| 2014/0074299 A1 | 3/2014 | Endou et al. | |
| 2014/0081394 A1 | 3/2014 | Keranen et al. | |
| 2014/0172070 A1 | 6/2014 | Seguin | |
| 2014/0194981 A1 | 7/2014 | Menk et al. | |
| 2014/0200661 A1 | 7/2014 | Pintor et al. | |
| 2014/0236287 A1 | 8/2014 | Clague et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2014/0358222 A1 | 12/2014 | Gorman, III et al. | |
| 2014/0379074 A1 | 12/2014 | Spence et al. | |
| 2015/0073545 A1 | 3/2015 | Braido | |
| 2015/0073546 A1 | 3/2015 | Braido | |
| 2015/0230921 A1 | 8/2015 | Chau et al. | |
| 2015/0282931 A1 | 10/2015 | Brunnett et al. | |
| 2015/0335428 A1 | 11/2015 | Keranen | |
| 2015/0335430 A1 | 11/2015 | Loulmet et al. | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0184095 A1 | 6/2016 | Spence et al. | |
| 2016/0199177 A1 | 7/2016 | Spence et al. | |
| 2016/0256276 A1 | 9/2016 | Yaron | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |
| 2017/0273788 A1 | 9/2017 | O'Carroll et al. | |
| 2018/0206074 A1 | 7/2018 | Tanasa et al. | |

FOREIGN PATENT DOCUMENTS

| | | |
|---|---|---|
| CN | 101588771 A | 11/2009 |
| DE | 19532846 A1 | 3/1997 |
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1432369 A1 | 6/2004 |

(56) References Cited

FOREIGN PATENT DOCUMENTS

| | | |
|---|---|---|
| EP | 1521550 A2 | 4/2005 |
| EP | 1796597 A2 | 6/2007 |
| EP | 1827314 A1 | 9/2007 |
| EP | 1296618 B1 | 1/2008 |
| EP | 2072027 A1 | 6/2009 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2788217 A1 | 7/2000 |
| FR | 2815844 A1 | 5/2002 |
| SU | 1271508 A1 | 11/1986 |
| WO | 1991017720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0203892 A1 | 1/2002 |
| WO | 0222054 A1 | 3/2002 |
| WO | 0236048 A1 | 5/2002 |
| WO | 0247575 A2 | 6/2002 |
| WO | 03028558 A2 | 4/2003 |
| WO | 03047468 A1 | 6/2003 |
| WO | 05/034812 | 4/2005 |
| WO | 2005084595 A1 | 9/2005 |
| WO | 2005102015 A2 | 11/2005 |
| WO | 2006011127 A2 | 2/2006 |
| WO | 2006/091163 A1 | 8/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 08058940 A1 | 5/2008 |
| WO | 2008091515 A2 | 7/2008 |
| WO | 2009033469 A1 | 3/2009 |
| WO | 2009134701 A2 | 11/2009 |
| WO | 2009155561 A2 | 12/2009 |
| WO | 2010057262 A1 | 5/2010 |
| WO | 2010121076 A2 | 10/2010 |
| WO | 2013001339 A2 | 1/2013 |
| WO | 2013068542 A1 | 5/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

OTHER PUBLICATIONS

Webb et al., "Transcatheter Valve-in-Valve Implantation for Failed Bioprosthetic Heart Valves," Journal of the American Heart Association, 11, Apr. 27, 2010.

Webb et al., "Mitral Valve in Valve," TCT Sep. 2009, Live Case: 30 Minutes, St. Paul's Hospital/University of British Columbia.

Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.

Cheung et al.,"Transapical Transcatheter Mitral Valve-in-Valve Implantation in a Human," The Society of Thoracic Surgeons, 2009.

Cheung et al, Live Case Transmissions, NYHA III CHF, Case Summary, Sep. 23, 2010, St. Paul's Hospital/University of British Columbia.

Shuto et al., "Percutaneous Transvenous Melody Valve-in-Ring Procedure for Mitral Valve Replacement," J Am Coll Cardiol, 58(24): 2475-2480, 2011.

Descoutures et al., "Transcatheter Valve-in-Ring Implantation After Failure of Surgical Mitral Repair," European Journal of Cardio-Thoracic Surgery 44, e8-e15, 2013.

Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.

Walther et al., "Human Minimally Invasive Off-Pump Valve-in-a-Valve Implantation," Case Reports, The Society of Thoracic Surgeons, 2008.

Walther et al., "Valve-in-a-Valve Concept for Transcatheter Minimally Invasive Repeat Xenograph Implantation," Preclinical Studies, Journal of the American College of Cardiology, 2007.

Himbert et al., "Transseptal Implantation of a Transcatheter Heart Valve in a Mitral Annuloplasty Ring to Treat Mitral Repair Failure," Circulation Cardiovascular Interventions, American Heart Association, 2011.

Himbert, Dominique, "Transvenous Mitral Valve Repair Replacement After Failure of Surgical Ring Annuloplasty," Research Correspondence, Journal of the American College of Cardiology, 2012.

Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.

Ma et al., "Double-Crowned Valved Stents for Off-Pump Mitral Valve Replacement," European Journal of Cardio-Thoracic Surgery, 28, 194-199, 2005.

Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.

International Search Report from corresponding PCT case No. PCT/IB2015/000901 dated Feb. 15, 2015.

Andersen, H.R., et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Andersen, H.R. "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 1 pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

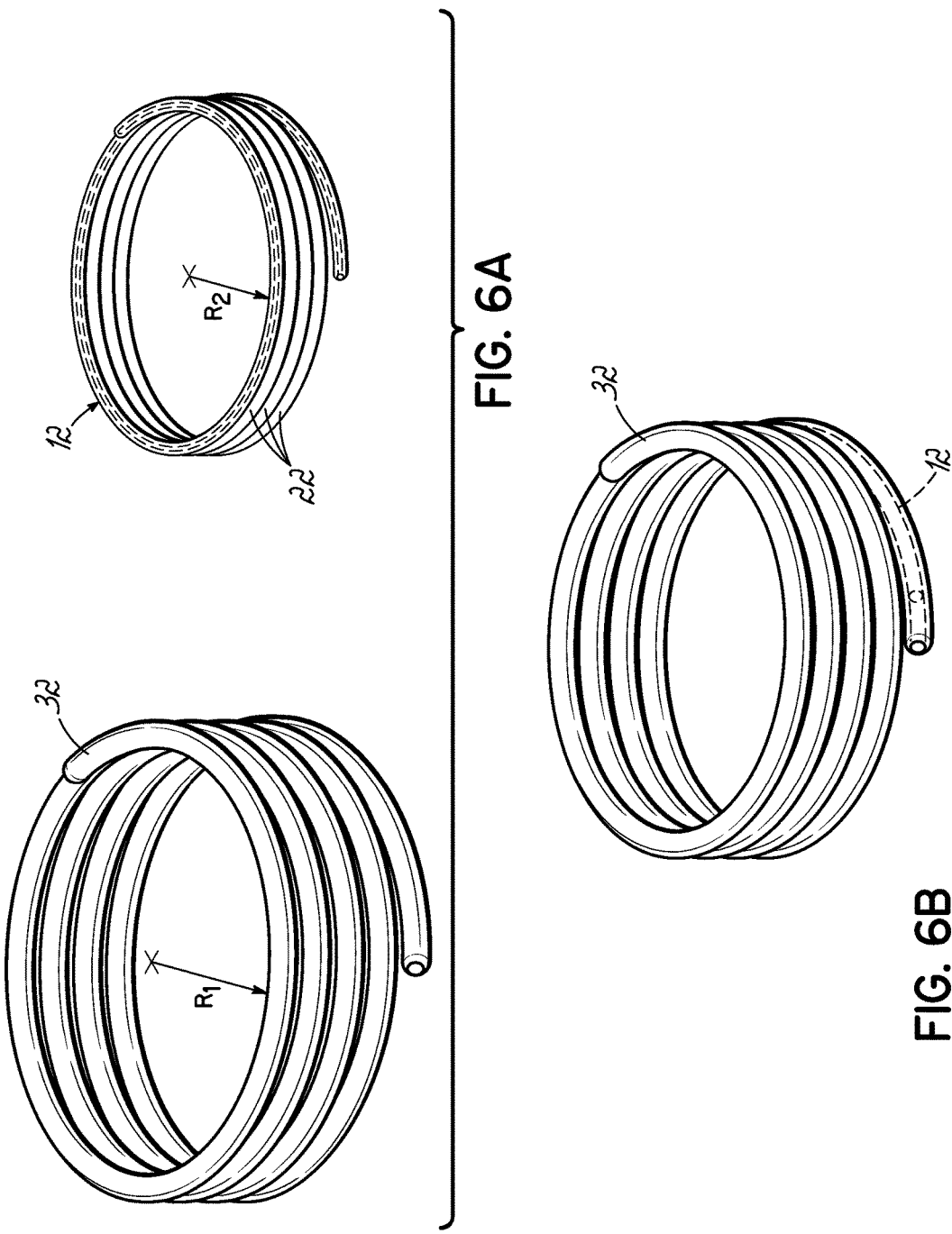

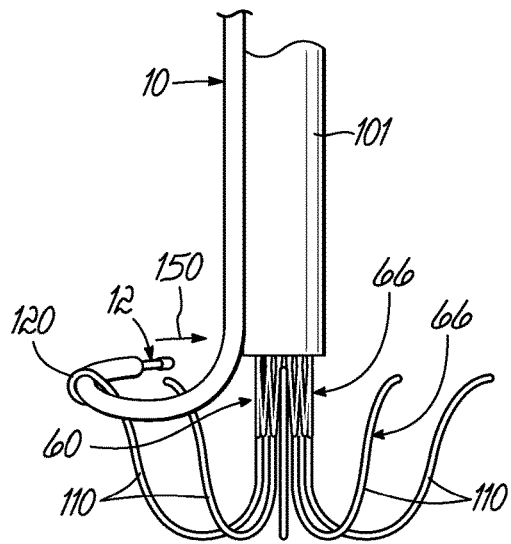
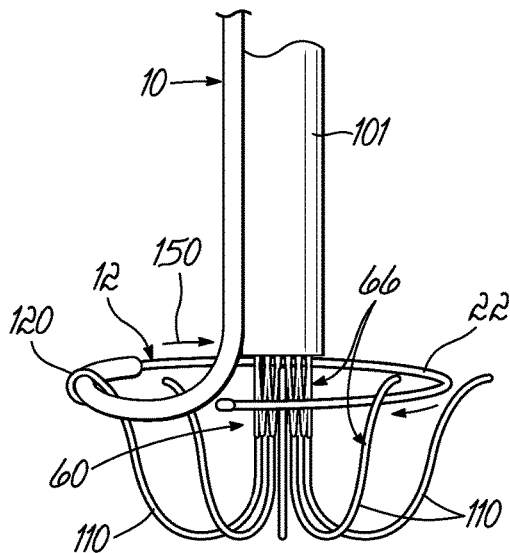
FIG. 18A
FIG. 18B
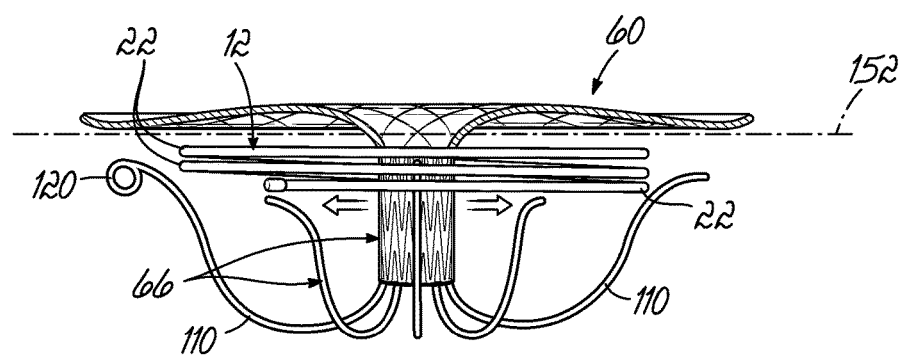
FIG. 18C

REPLACEMENT HEART VALVE APPARATUS AND METHODS

CROSS-REFERENCE TO RELATED APPLICATIONS

This application claims the priority of U.S. Provisional Application Ser. No. 61/865,657, filed Aug. 14, 2013; U.S. Provisional Application Ser. No. 61/942,300, filed Feb. 20, 2014; and U.S. Provisional Application Ser. No. 61/943,125, filed Feb. 21, 2014, the disclosures of which are hereby incorporated by reference herein.

TECHNICAL FIELD

The present invention generally relates to medical procedures and devices pertaining to heart valves such as replacement techniques and apparatus. More specifically, the invention relates to the replacement of heart valves having various malformations and dysfunctions.

BACKGROUND

Complications of the mitral valve, which controls the flow of blood from the left atrium into the left ventricle of the human heart, have been known to cause fatal heart failure. In the developed world, one of the most common forms of valvular heart disease is mitral valve leak, also known as mitral regurgitation, which is characterized by the abnormal leaking of blood from the left ventricle through the mitral valve and back into the left atrium. This occurs most commonly due to ischemic heart disease when the leaflets of the mitral valve no longer meet or close properly after multiple infarctions, idiopathic and hypertensive cardiomyopathies where the left ventricle enlarges, and with leaflet and chordal abnormalities, such as those caused by a degenerative disease.

In addition to mitral regurgitation, mitral narrowing or stenosis is most frequently the result of rheumatic disease. While this has been virtually eliminated in developed countries, it is still common where living standards are not as high.

Similar to complications of the mitral valve are complications of the aortic valve, which controls the flow of blood from the left ventricle into the aorta. For example, many older patients develop aortic valve stenosis. Historically, the traditional treatment had been valve replacement by a large open heart procedure. The procedure takes a considerable amount of time for recovery since it is so highly invasive. Fortunately, in the last decade, great advances have been made in replacing this open heart surgery procedure with a catheter procedure that can be performed quickly without surgical incisions or the need for a heart-lung machine to support the circulation while the heart is stopped. Using catheters, valves are mounted on stents or stent-like structures, which are compressed and delivered through blood vessels to the heart. The stents are then expanded and the valves begin to function. The diseased valve is not removed, but instead it is crushed or deformed by the stent which contains the new valve. The deformed tissue serves to help anchor the new prosthetic valve.

Delivery of the valves can be accomplished from arteries which can be easily accessed in a patient. Most commonly this is done from the groin where the femoral and iliac arteries can be cannulated. The shoulder region is also used, where the subclavian and axillary arteries can also be accessed. Recovery from this procedure is remarkably quick.

Not all patients can be served with a pure catheter procedure. In some cases the arteries are too small to allow passage of catheters to the heart, or the arteries are too diseased or tortuous. In these cases, surgeons can make a small chest incision (thoractomy) and then place these catheter-based devices directly into the heart. Typically, a purse string suture is made in the apex of the left ventricle and the delivery system is placed through the apex of the heart. The valve is then delivered into its final position. These delivery systems can also be used to access the aortic valve from the aorta itself. Some surgeons introduce the aortic valve delivery system directly in the aorta at the time of open surgery. The valves vary considerably. There is a mounting structure that is often a form of stent. Prosthetic leaflets are carried inside the stent on mounting and retention structure. Typically, these leaflets are made from biologic material that is used in traditional surgical valves. The valve can be actual heart valve tissue from an animal or more often the leaflets are made from pericardial tissue from cows, pigs or horses. These leaflets are treated to reduce their immunogenicity and improve their durability. Many tissue processing techniques have been developed for this purpose. In the future, biologically engineered tissue may be used or polymers or other non-biologic materials may be used for valve leaflets. All of these can be incorporated into the inventions described in this disclosure.

There are, in fact, more patients with mitral valve disease than aortic valve disease. In the course of the last decade, many companies have been successful in creating catheter or minimally invasive implantable aortic valves, but implantation of a mitral valve is more difficult and to date there has been no good solution. Patients would be benefited by implanting a device by a surgical procedure employing a small incision or by a catheter implantation such as from the groin. From the patient's point of view, the catheter procedure is very attractive. At this time there is no commercially available way to replace the mitral valve with a catheter procedure. Many patients who require mitral valve replacement are elderly and an open heart procedure is painful, risky and takes time for recovery. Some patients are not even candidates for surgery due to advanced age and frailty. Therefore, there exists a particular need for a remotely placed mitral valve replacement device.

While previously, it was thought that mitral valve replacement rather than valve repair was associated with a more negative long-term prognosis for patients with mitral valve disease, this belief has come into question. It is now believed that the outcome for patients with mitral valve leak or regurgitation is almost equal whether the valve is repaired or replaced. Furthermore, the durability of a mitral valve surgical repair is now under question. Many patients, who have undergone repair, redevelop a leak over several years. As many of these are elderly, a repeat intervention in an older patient is not welcomed by the patient or the physicians.

The most prominent obstacle for catheter mitral valve replacement is retaining the valve in position. The mitral valve is subject to a large cyclic load. The pressure in the left ventricle is close to zero before contraction and then rises to the systolic pressure (or higher if there is aortic stenosis) and this can be very high if the patient has systolic hypertension. Often the load on the valve is 150 mmHg or more. Since the heart is moving as it beats, the movement and the load can combine to dislodge a valve. Also, the movement and rhythmic load can fatigue materials leading to fractures of the materials. Thus, there is a major problem associated with anchoring a valve.

Another problem with creating a catheter delivered mitral valve replacement is size. The implant must have strong retention and leak avoidance features and it must contain a valve. Separate prostheses may contribute to solving this problem, by placing an anchor or dock first and then implanting the valve second. However, in this situation, the patient must remain stable between implantation of the anchor or dock and implantation of the valve. If the patient's native mitral valve is rendered non-functional by the anchor or dock, then the patient may quickly become unstable and the operator may be forced to hastily implant the new valve or possibly stabilize the patient by removing the anchor or dock and abandoning the procedure.

Another problem with mitral replacement is leak around the valve, or paravalvular leak. If a good seal is not established around the valve, blood can leak back into the left atrium. This places extra load on the heart and can damage the blood as it travels in jets through sites of leaks. Hemolysis or breakdown of red blood cells is a frequent complication if this occurs. Paravalvular leak was one of the common problems encountered when the aortic valve was first implanted on a catheter. During surgical replacement, a surgeon has a major advantage when replacing the valve as he or she can see a gap outside the valve suture line and prevent or repair it. With catheter insertion, this is not possible. Furthermore, large leaks may reduce a patient's survival and may cause symptoms that restrict mobility and make the patient uncomfortable (e.g., short of breathe, edematous, fatigued). Therefore, devices, systems, and methods which relate to mitral valve replacement should also incorporate means to prevent and repair leaks around the replacement valve.

A patient's mitral valve annulus can also be quite large. When companies develop surgical replacement valves, this problem is solved by restricting the number of sizes of the actual valve produced and then adding more fabric cuff around the margin of the valve to increase the valve size. For example, a patient may have a 45 mm valve annulus. In this case, the actual prosthetic valve diameter may be 30 mm and the difference is made up by adding a larger band of fabric cuff material around the prosthetic valve. However, in catheter procedures, adding more material to a prosthetic valve is problematic since the material must be condensed and retained by small delivery systems. Often, this method is very difficult and impractical, so alternative solutions are necessary.

Since numerous valves have been developed for the aortic position, it is desirable to avoid repeating valve development and to take advantage of existing valves. These valves have been very expensive to develop and bring to market, so extending their application can save considerable amounts of time and money. It would be useful then to create a mitral anchor or docking station for such a valve. An existing valve developed for the aortic position, perhaps with some modification, could then be implanted in the docking station. Some previously developed valves may fit well with no modification, such as the Edwards Sapien™ valve. Others, such as the Corevalve™ may be implantable but require some modification for an optimal engagement with the anchor and fit inside the heart.

A number of further complications may arise from a poorly retained or poorly positioned mitral valve replacement prosthesis. Namely, a valve can be dislodged into the atrium or ventricle, which could be fatal for a patient. Prior prosthetic anchors have reduced the risk of dislodgement by puncturing tissue to retain the prosthesis. However, this is a risky maneuver since the penetration must be accomplished by a sharp object at a long distance, leading to a risk of perforation of the heart and patient injury.

Orientation of the mitral prosthesis is also important. The valve must allow blood to flow easily from the atrium to the ventricle. A prosthesis that enters at an angle may lead to poor flow, obstruction of the flow by the wall of the heart or a leaflet and a poor hemodynamic result. Repeated contraction against the ventricular wall can also lead to rupture of the back wall of the heart and sudden death of the patient.

With surgical mitral valve repair or replacement, sometimes the anterior leaflet of the mitral valve leaflet is pushed into the area of the left ventricular outflow and this leads to poor left ventricular emptying. This syndrome is known as left ventricular tract outflow obstruction. The replacement valve itself can cause left ventricular outflow tract obstruction if it is situated close to the aortic valve.

Yet another obstacle faced when implanting a replacement mitral valve is the need for the patient's native mitral valve to continue to function regularly during placement of the prosthesis so that the patient can remain stable without the need for a heart-lung machine to support circulation.

In addition, it is desirable to provide devices and methods that can be utilized in a variety of implantation approaches. Depending on a particular patient's anatomy and clinical situation, a medical professional may wish to make a determination regarding the optimal method of implantation, such as inserting a replacement valve directly into the heart in an open procedure (open heart surgery or a minimally invasive surgery) or inserting a replacement valve from veins and via arteries in a closed procedure (such as a catheter-based implantation). It is preferable to allow a medical professional a plurality of implantation options to choose from. For example, a medical professional may wish to insert a replacement valve either from the ventricle or from the atrial side of the mitral valve.

Therefore, the present invention provides devices and methods that address these and other challenges in the art.

SUMMARY

In one illustrative embodiment, the invention provides a system for replacing a native heart valve including an expansible helical anchor formed as multiple coils adapted to support a heart valve prosthesis. At least one of the coils is normally at a first diameter, and is expandable to a second, larger diameter upon application of radial outward force from within the helical anchor. A gap is defined between adjacent coils sufficient to prevent engagement by at least one of the adjacent coils with the native heart valve. An expansible heart valve prosthesis is provided and is configured to be delivered into the helical anchor and expanded inside the multiple coils into engagement with the at least one coil. This moves at least that coil from the first diameter to the second diameter while securing the helical anchor and the heart valve prosthesis together. The system further includes a seal on the expansible heart valve prosthesis configured to engage the helical anchor and prevent blood leakage past the heart valve prosthesis after implantation of the heart valve prosthesis in the helical anchor.

The system may include one or more additional aspects. For example, the helical anchor may include another coil that moves from a larger diameter to a smaller diameter as the heart valve prosthesis is expanded inside the multiple coils. The seal may take many alternative forms. For example, the seal can include portions extending between adjacent coils for preventing blood leakage through the helical anchor and past the heart valve prosthesis. The seal may be comprised of many different alternative materials. The seal may further comprise a membrane or panel extending between at least two coils of the helical anchor after implantation of the heart valve prosthesis in the helical anchor. For example, one example is a biologic material. The helical anchor may further comprise a shape memory material. The heart valve prosthesis includes a blood inflow end and a blood outflow end and at least one of the ends may be unflared and generally cylindrical in shape. In an illustrative embodiment, the blood outflow end is flared radially outward and includes a bumper for preventing damage to tissue structure in the heart after implantation. The gap may be formed by a coil portion of the helical anchor that extends non-parallel to adjacent coil portions of the helical anchor.

In another illustrative embodiment, a system is provided as generally described above, except that the seal is alternatively or additionally carried on the helical anchor instead of being carried on the heart valve prosthesis. Any other features as described or incorporated herein may be included.

In another illustrative embodiment, a system for docking a heart valve prosthesis includes a helical anchor formed as multiple coils adapted to support a heart valve prosthesis with coil portions positioned above and/or below the heart valve annulus. An outer, flexible and helical tube carries the coils of the helical anchor to form an assembly. A helical delivery tool carries the assembly and is adapted to be rotated into position through a native heart valve. Additional or optional features may be provided. For example, a heart valve prosthesis may be expanded inside the multiple coils. The outer tube may be formed from a low friction material adapted to slide off of the multiple coils of the helical anchor after rotating into position through the native heart valve. The outer tube may be secured to the helical delivery tool with suture or by any other method. The helical delivery tool may formed with a plurality of coils, and the outer tube may further be secured to the distal end. The distal end may further comprise a bullet or tapered shape to assist with delivery. The distal end can further comprise a resilient element, and the distal ends of the outer tube and the helical delivery tube are secured to the resilient element.

In another illustrative embodiment, a system for replacing a native heart valve includes a helical anchor formed as multiple coils adapted to support a heart valve prosthesis at the native heart valve. An expansible heart valve prosthesis is provided in this system and is capable of being delivered into the helical anchor and expanded inside the multiple coils into engagement with the at least one coil to secure the helical anchor and the heart valve prosthesis together. A guide structure on the expansible heart valve prosthesis is configured to guide the helical anchor into position as the helical anchor is extruded from a helical anchor delivery catheter.

The guide structure may further comprise an opening within a portion of the expansible heart valve prosthesis, such as an opening in a loop, a tube or simply an opening in the stent structure of the expansible heart valve prosthesis, for example. The opening may be configured to receive a helical anchor delivery catheter that carries the helical anchor during the implantation procedure. The opening may be located on an arm of the expansible heart valve prosthesis and the prosthesis may further comprise a plurality of arms configured to engage beneath the native heart valve. The guide structure may further comprise a tubular arm of the expansible heart valve prosthesis.

In another illustrative embodiment, a system for docking a mitral valve prosthesis and replacing a native mitral valve is provided and includes a coil guide catheter and a helical anchor adapted to be received in and delivered from the coil guide catheter. The helical anchor is formed as multiple coils having a coiled configuration after being delivered from the coil guide catheter and adapted to support the mitral valve prosthesis upon being fully delivered from the coil guide catheter and implanted at the native mitral valve. The system further includes a tissue gathering catheter including loop structure configured to be deployed to surround and gather the native chordea tendinae for allowing easier direction of the helical anchor in the left ventricle.

In another illustrative embodiment, an anchor for docking a heart valve prosthesis includes an upper helical coil portion, a lower helical coil portion, and a fastener securing the upper helical coil portion to the lower helical coil portion.

In another illustrative embodiment, a method of implanting a heart valve prosthesis in the heart of a patient includes holding a helical anchor in the form of multiple coils within an outer, flexible tube. The assembly of the outer, flexible tube and the helical anchor is secured to a helical delivery tool. The helical delivery tool is rotated adjacent to a native heart valve of the patient to position the assembly on either or both sides of the native heart valve. The assembly is removed from the helical delivery tool, and the outer tube is removed from the helical anchor. The heart valve prosthesis is then implanted within the helical anchor.

Securing the assembly may further comprise positioning coils of the assembly generally along adjacent coils of the helical delivery tool. Removing the outer tube may further comprise holding the helical anchor with a pusher element, and pulling the outer tube off the helical anchor.

In another illustrative embodiment, a method of implanting an expansible heart valve prosthesis in the heart of a patient includes delivering an expansible helical anchor in the form of multiple coils proximate the native heart valve. The expansible heart valve prosthesis is positioned within the multiple coils of the expansible helical anchor with the expansible heart valve prosthesis and the expansible helical anchor in unexpanded states. The expansible heart valve prosthesis is expanded against the expansible helical anchor thereby expanding the expansible heart valve prosthesis while securing the expansible heart valve prosthesis to the expansible helical anchor. A seal is carried on the helical anchor and/or on the heart valve prosthesis and extends between at least two adjacent coils for preventing blood leakage through the helical anchor and past the heart valve prosthesis.

In another illustrative embodiment, a method of implanting an expansible heart valve prosthesis to replace a native heart valve of a patient includes delivering a helical anchor in the form of multiple coils proximate the native heart valve. The expansible heart valve prosthesis is delivered proximate the native heart valve. The helical anchor is guided generally around a periphery of the expansible heart valve prosthesis using guide structure carried on the expansible heart valve prosthesis. The expansible heart valve prosthesis is expanded against the helical anchor. As discussed above, the guide structure may take many different forms.

In another illustrative embodiment, a method of implanting a helical anchor for docking a mitral heart valve prosthesis in a patient includes gathering the chordea tendinae using a tissue gathering catheter. A helical anchor is then delivered in the form of multiple coils proximate a native heart valve and around the gathered chordae tendinae.

In another illustrative embodiment, a method of implanting a helical anchor for docking a heart valve prosthesis in a patient includes delivering an upper helical anchor portion comprised of upper coils to a position above a native heart valve, and delivering a lower helical anchor portion comprised of lower coils to a position below the native heart valve. The upper and lower helical anchor portions are secured together with a fastener either before or after delivery of each helical anchor portion.

In another illustrative embodiment, a system for replacing a native heart valve is provided and includes an expansible helical anchor formed as multiple coils adapted to support a heart valve prosthesis. At least one of the coils is normally at a first diameter, and is expandable to a second, larger diameter upon application of radial outward force from within the helical anchor. A gap is defined between adjacent coils sufficient to prevent engagement by at least one of the adjacent coils with the native heart valve. An expansible heart valve prosthesis is provided and is capable of being delivered into the helical anchor and expanded inside the multiple coils into engagement with the at least one coil. In this manner, the expansible coil moves from the first diameter to the second diameter while securing the helical anchor and the heart valve prosthesis together. The expansible heart valve prosthesis includes an inflow end and an outflow end. The inflow end is unflared and generally cylindrical, while the outflow end is flared in a radially outward direction.

Various additional advantages, methods, devices, systems and features will become more readily apparent to those of ordinary skill in the art upon review of the following detailed description of the illustrative embodiments taken in conjunction with the accompanying drawings.

BRIEF DESCRIPTION OF THE DRAWINGS

FIG. 6A is a perspective view showing the combination of a helical anchor and an outer tube used for assisting with the delivery of the helical anchor to the native mitral valve location.

FIG. 6B is a perspective view of the helical anchor within the outer tube shown in FIG. 6A.

FIGS. 18A, 18B and 18C are views similar to FIGS. 16A and 16B, however, these views progressively illustrate another embodiment of a method for deploying a helical anchor and a stent mounted replacement heart valve.

DETAILED DESCRIPTION OF THE ILLUSTRATIVE EMBODIMENTS

Figure 1:
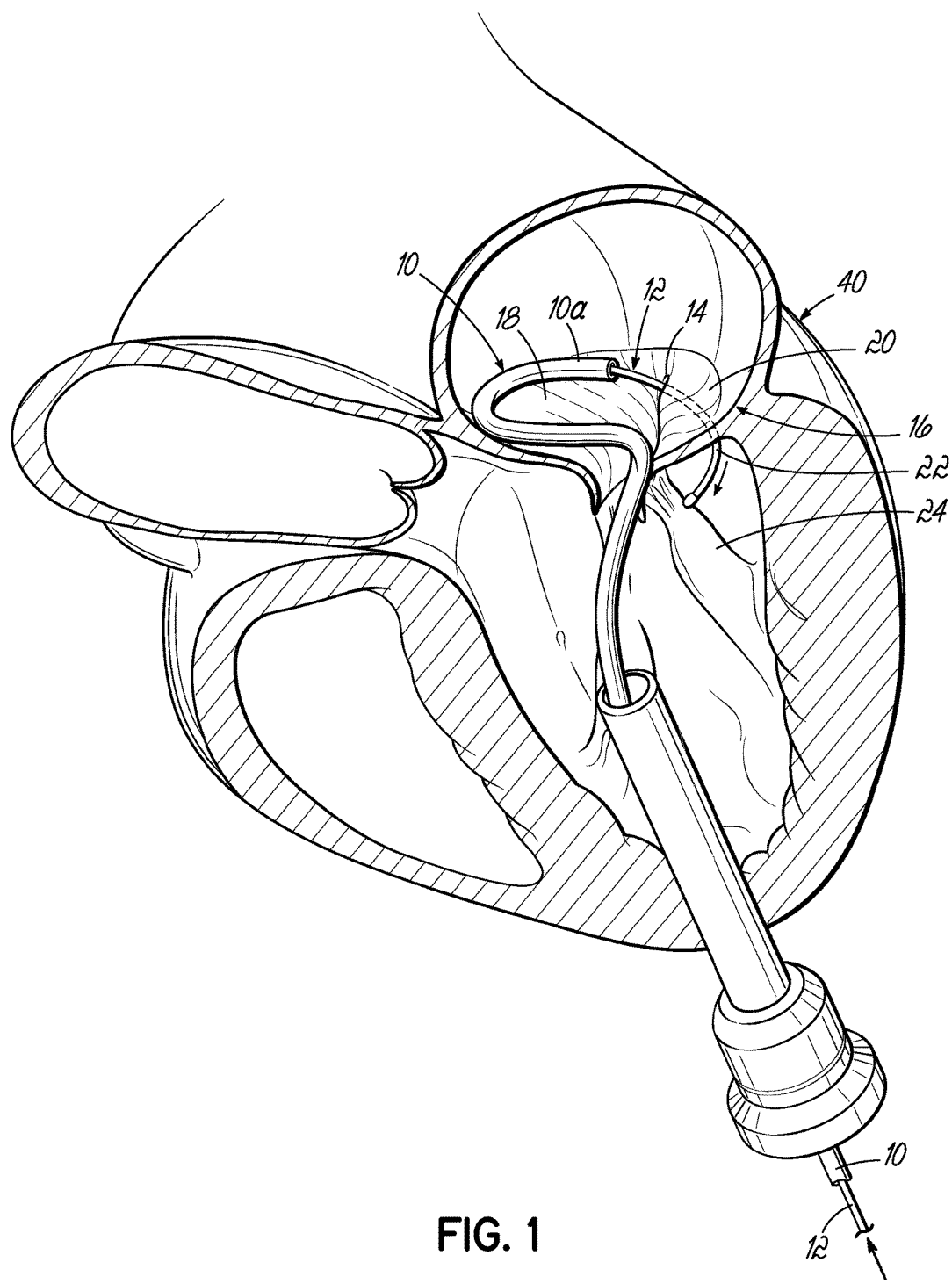
FIG. 1 is a perspective view schematically illustrating the introduction of a helical anchor to the position of the native mitral valve.

It will be appreciated that like reference numerals throughout this description and the drawings refer generally to like elements of structure and function. The differences between embodiments will be apparent from the drawings and/or from the description and/or the use of different reference numerals in different figures. For clarity and conciseness, description of like elements will not be repeated throughout the description.

Figure 2A:
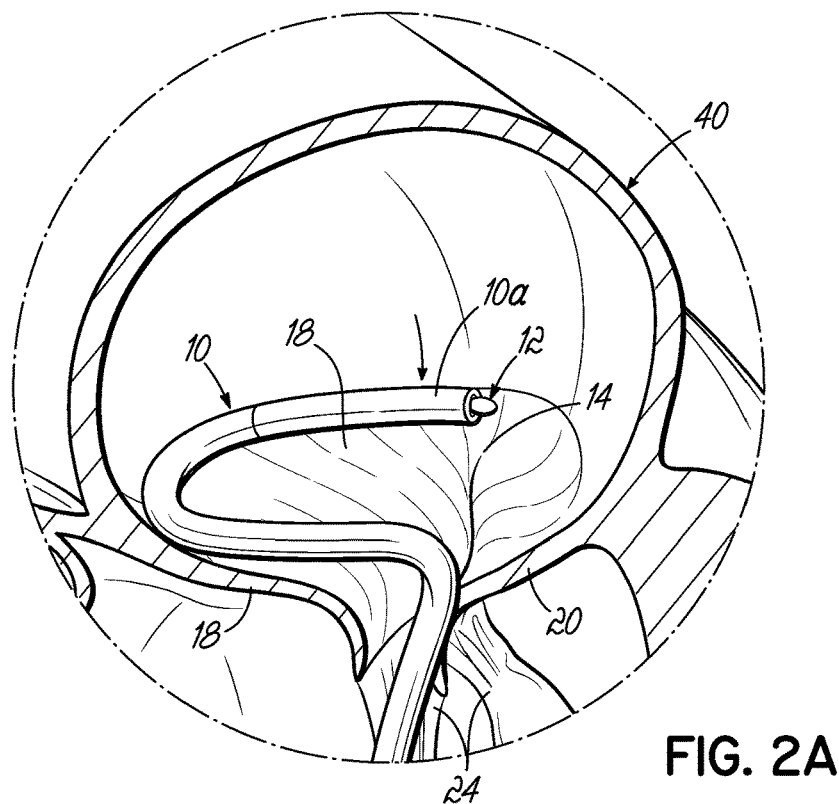
FIG. 2A is an enlarged cross-sectional view illustrating an initial portion of the procedure shown in FIG. 1, but with use of a deflectable catheter.
Figure 2B:
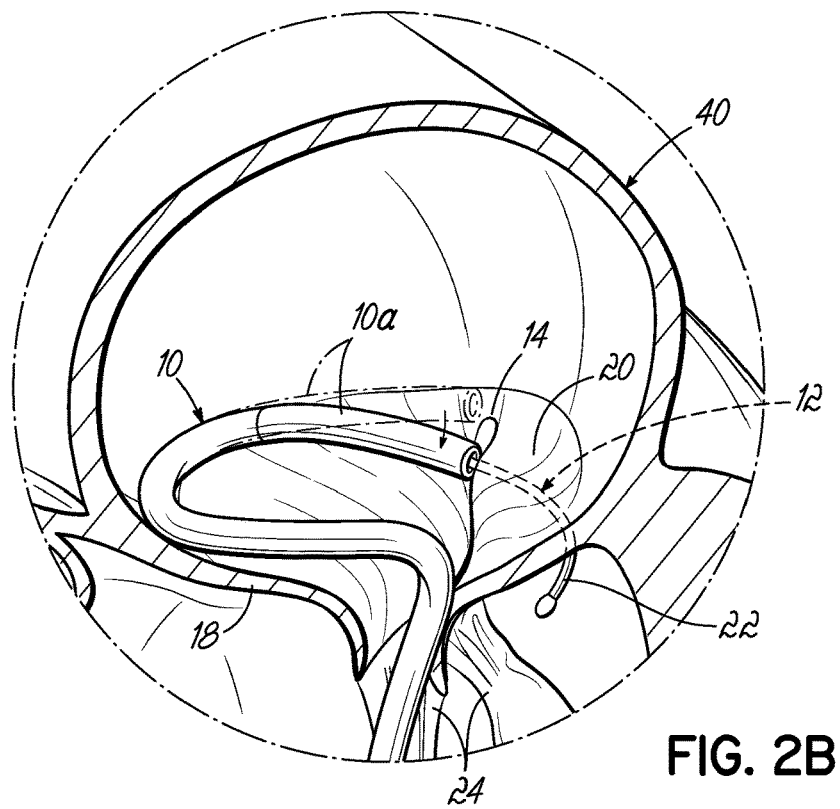
FIG. 2B is a cross-sectional view of the heart similar to FIG. 2A, but illustrating deflection of the delivery catheter and introduction of the helical anchor underneath the native mitral valve.
Figure 3A:
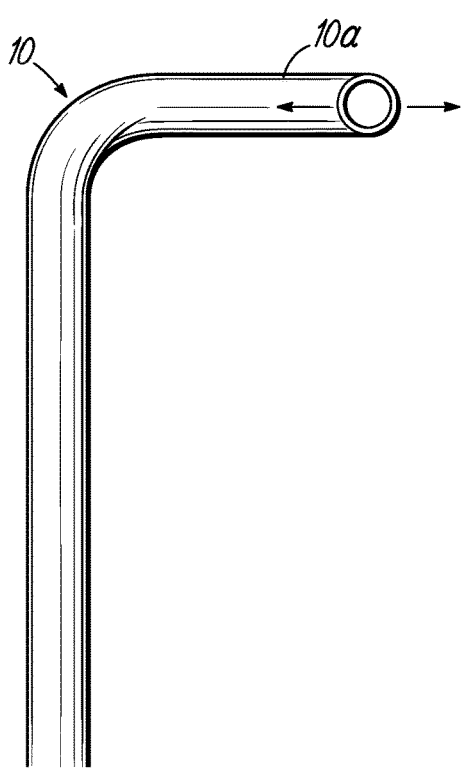
FIGS. 3A and 3B are enlarged elevational views illustrating the distal end of the delivery catheter and its deflecting capability.
Figure 3B:
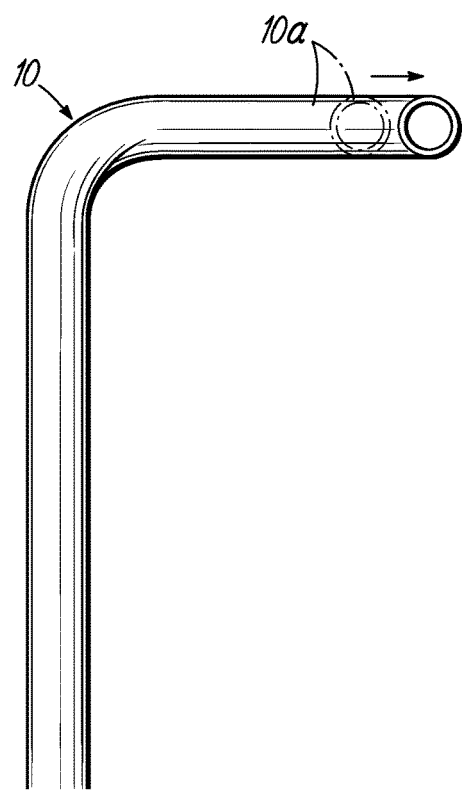
Figure 4A:
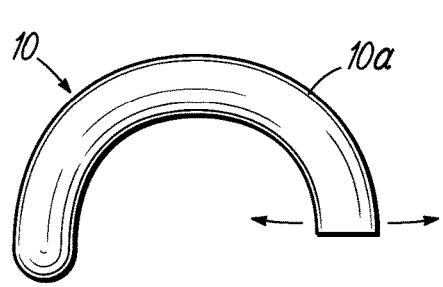
FIGS. 4A and 4B are respective top views of FIGS. 3A and 3B.
Figure 4B:
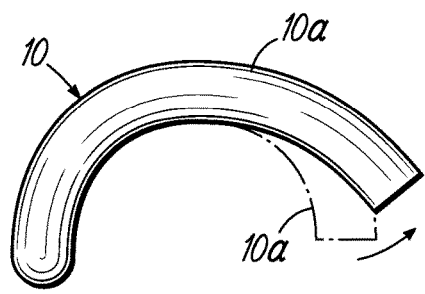
Figure 5A:
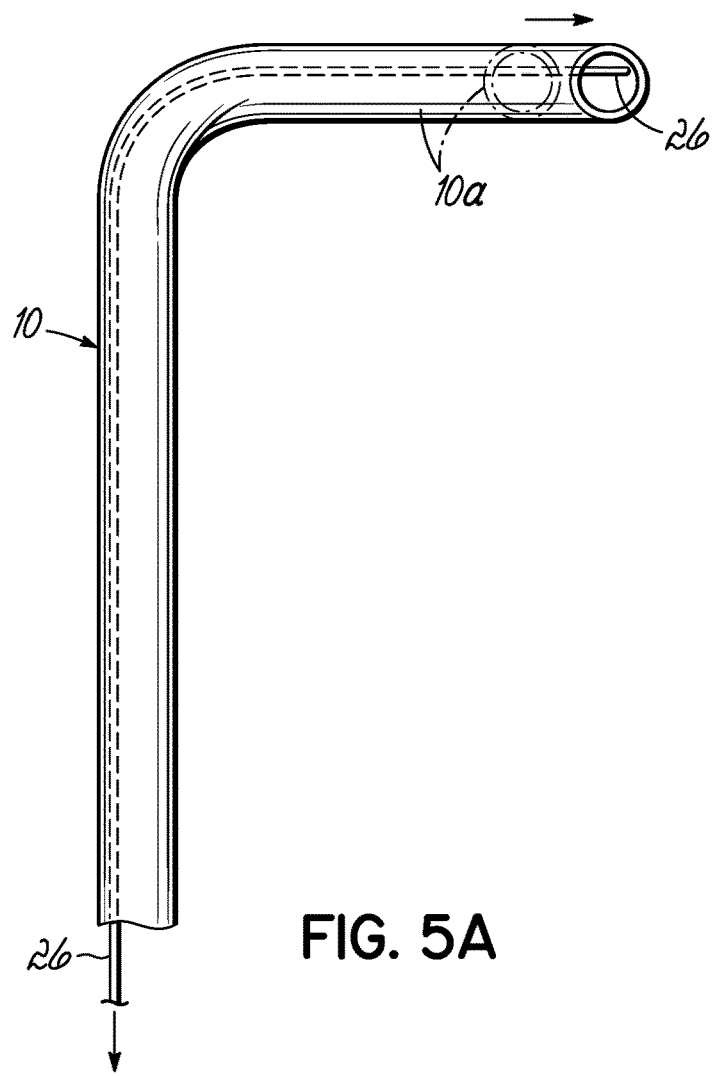
FIG. 5A is a side elevational view similar to FIG. 3B, but illustrating the use of a wire within the delivery catheter used for deflecting or steering the distal end.
Figure 5B:
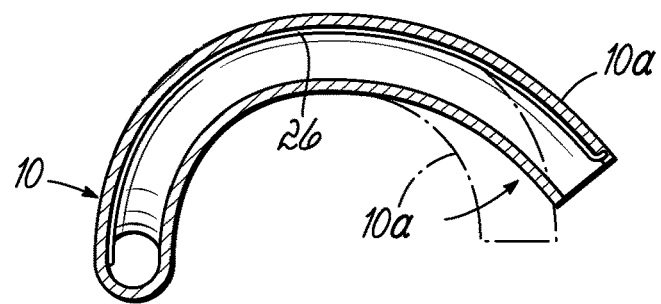
FIG. 5B is a cross-sectional, top view of the delivery catheter shown in FIG. 5A.
Figure 7A:
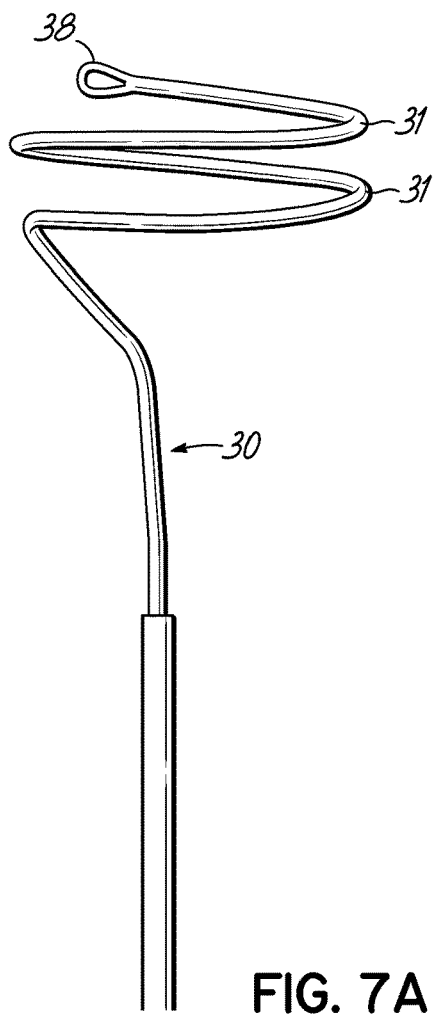
FIG. 7A is an elevational view showing a helical delivery tool used to deliver the assembly of FIG. 6B to the native mitral valve location.
Figure 7B:
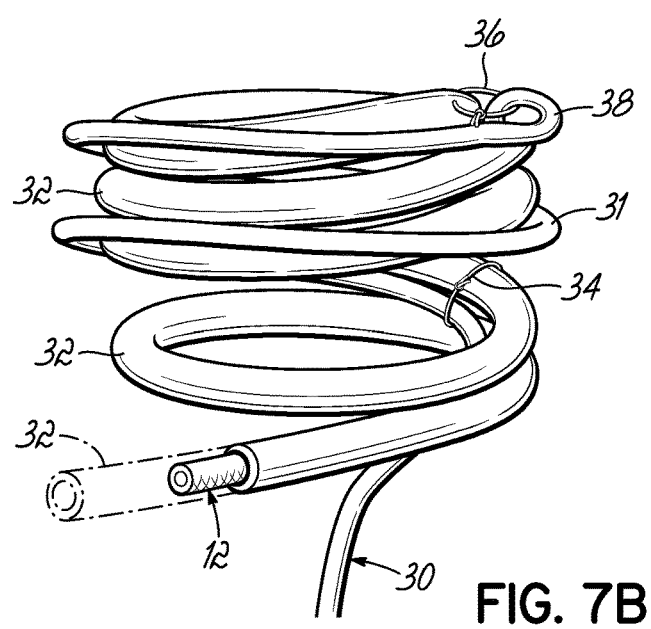
FIG. 7B is a perspective view illustrating the attachment of the assembly shown in FIG. 6B to the helical delivery tool shown in FIG. 7A.

Referring first to FIG. 1 in conjunction with FIGS. 2A and 2B, as previously discussed in Applicant's PCT Application Serial No. PCT/US2013/024114, the disclosure of which is fully incorporated by reference herein, a deflectable catheter 10 makes implantation of a helical anchor 12 much easier. The deflectable tip 10a of the catheter 10 assists with the helical anchor 12 engaging a commissure 14 of the native mitral valve 16, as shown in FIG. 1. The tip 10a of the catheter 10 may be designed and configured such that it can bend downward toward the native leaflets 18, 20 of the mitral valve 16. Once the tip 10a of the catheter 10 is placed generally over the commissure 14 as shown in FIG. 2A, the tip or distal end 10a may be bent downward and it is then relatively easy to push or extrude the helical anchor 12 out of the distal end 10a and downward through the mitral valve 16 as shown in FIG. 2B.

Now referring to FIGS. 3A, 3B, 4A, 4B, 5A and 5B, the deflectable catheter, or anchor delivery catheter 10, may be deflectable at many different points or locations. Deflecting the catheter tip 10a outward to increase the radius of the delivery catheter tip 10a can be very helpful, as shown in FIGS. 3A, 3B and 4A, 4B which show the "before" and "after" effects of deflecting the distal end 10a. Deflecting the catheter 10 in this way will give the helical anchor 12 a larger diameter starting turn or coil 22. As an example, this turn or coil 22 of the helical anchor 12 may normally be 25 mm but operating the distal end 10a of the catheter 10 in this manner can enlarge the diameter to 30 mm. Opening up the first turn or coil 22 of the helical anchor 12 in this way would help the helical anchor 12 capture all chordae 24 and leaflets 18, 20 as the helical anchor 12 is introduced as generally discussed above in connection with FIG. 1 and FIGS. 2A and 2B. As the helical anchor 12 advances, the distal end 10a of the delivery catheter 10 could also deflect inward to help the helical anchor 12 capture all of the chordae 24 at the opposite commissure. Moving the distal end 10a of the delivery catheter 10 from side to side as the helical anchor 12 is essentially screwed or rotated into and through the native mitral valve 16 is essentially like tracking the delivery catheter 10 with the turn or coil 22. In this case, however, the delivery catheter 10 is stationary as only the tip 10a is moving with the coils 22. Deflectability of the distal end 10a in any direction may be achieved by embedding a wire 26 that runs the length of the delivery catheter 10. When the wire 26 is pulled, the delivery catheter tip 10a deflects and deforms into various shapes as desired or needed in the procedure.

Figure 8A:
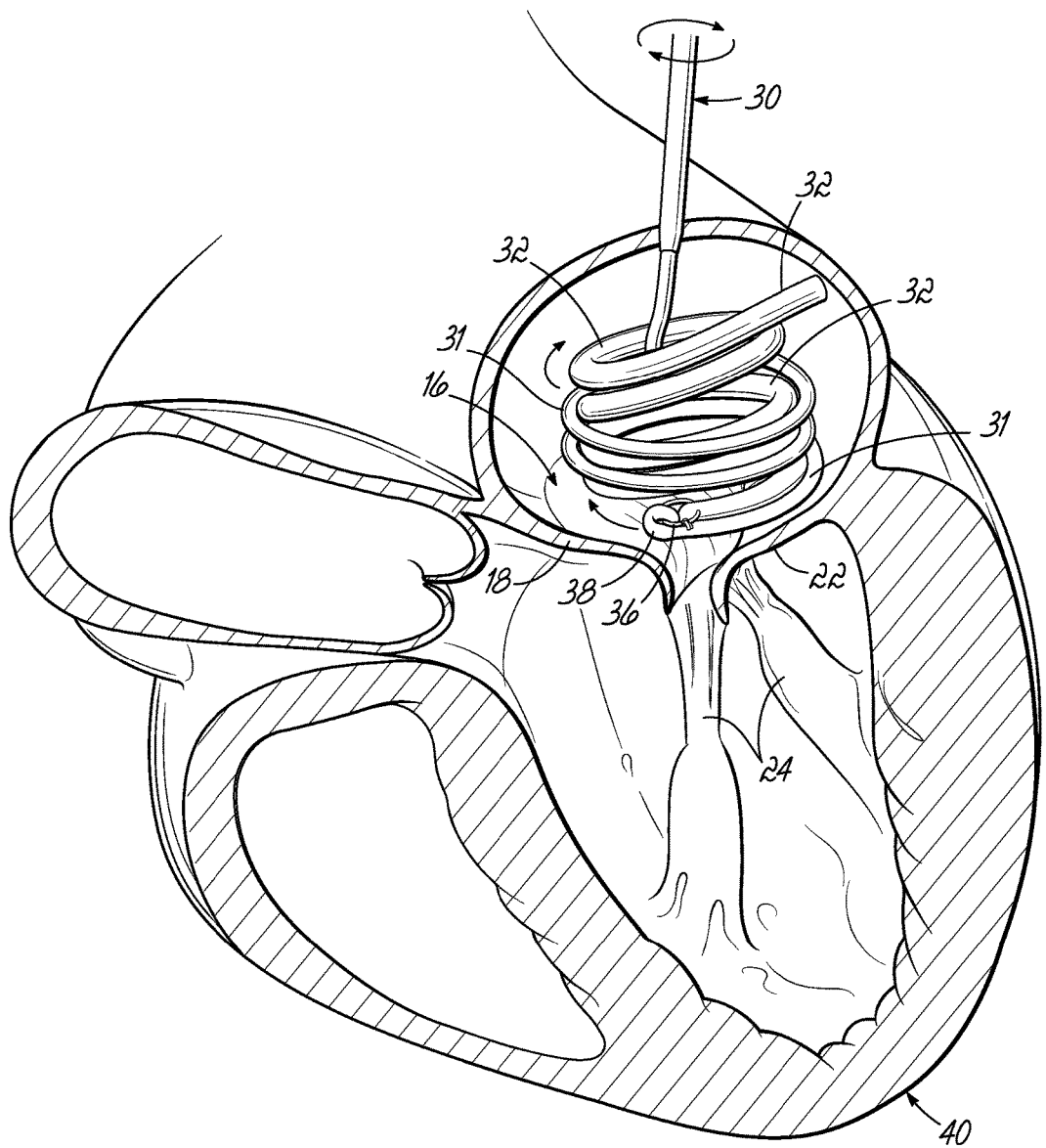
FIG. 8A is a perspective view showing the heart in cross section and the helical delivery tool being used to implant the assembly of FIG. 6B.
Figure 8B:
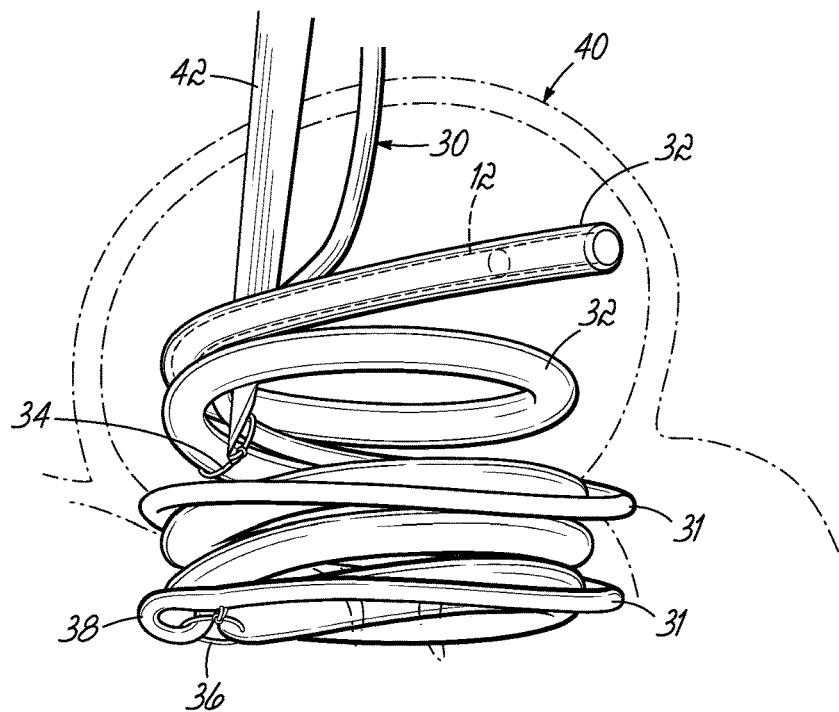
FIGS. 8B through 8E are perspective views showing further steps in the method of implantation.
Figure 8C:
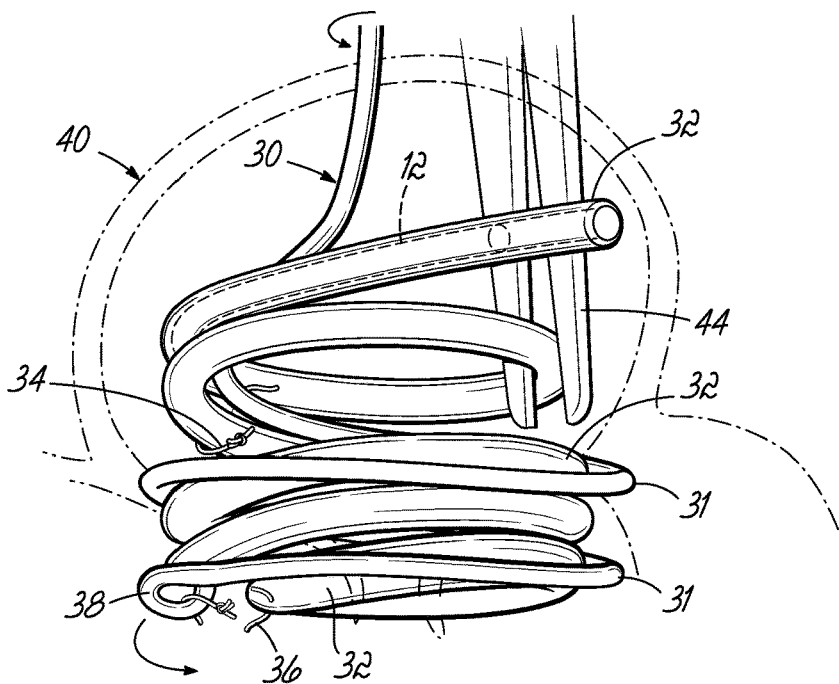
Figure 8D:
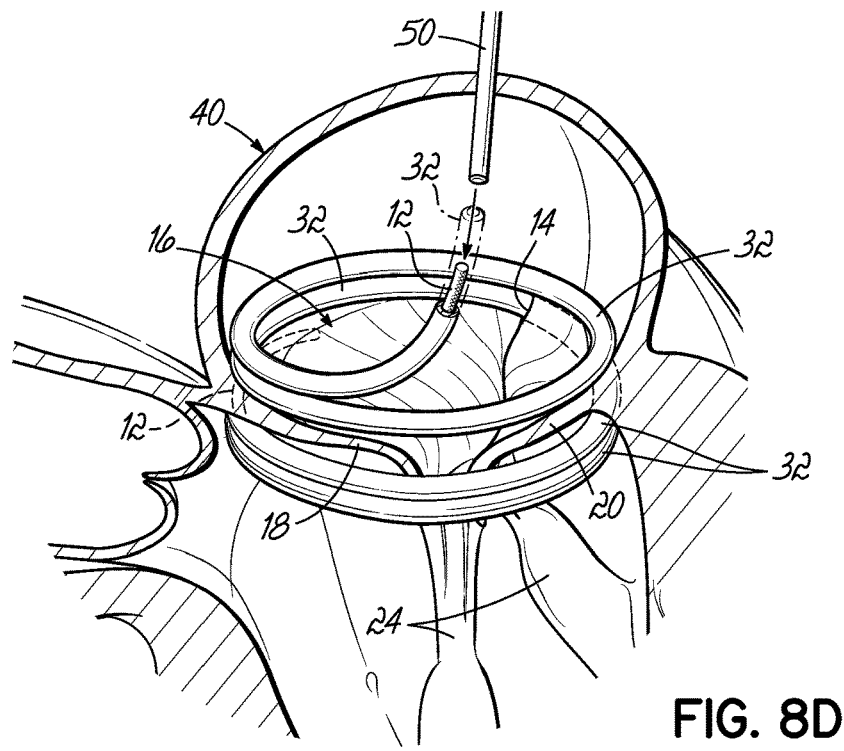
Figure 8E:
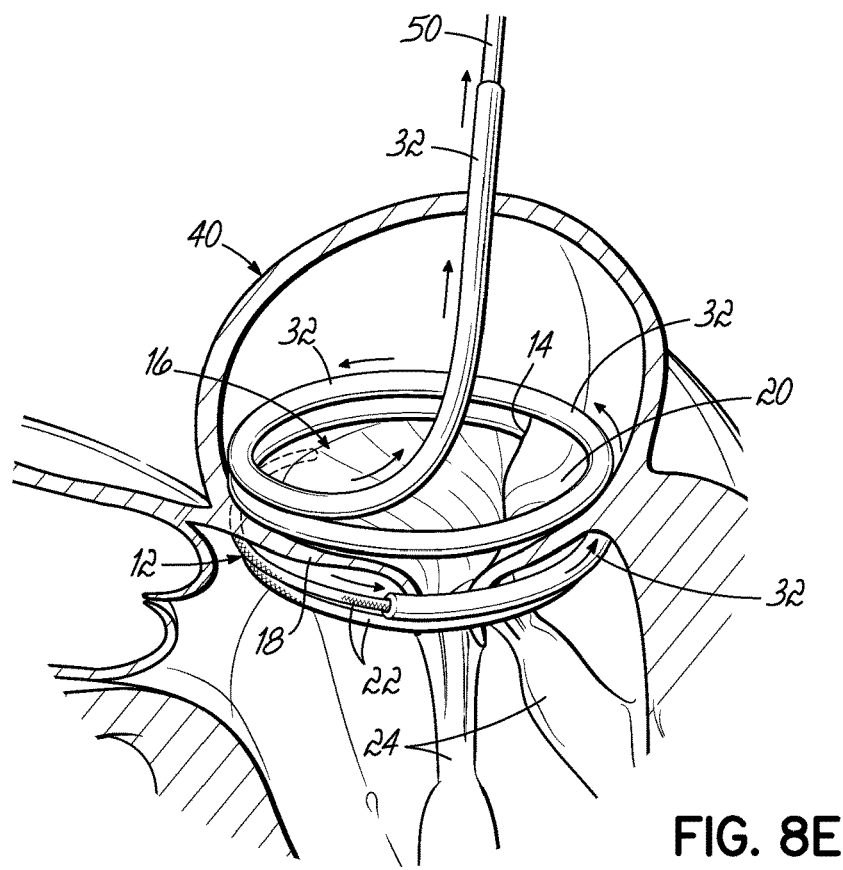
Figure 8F:
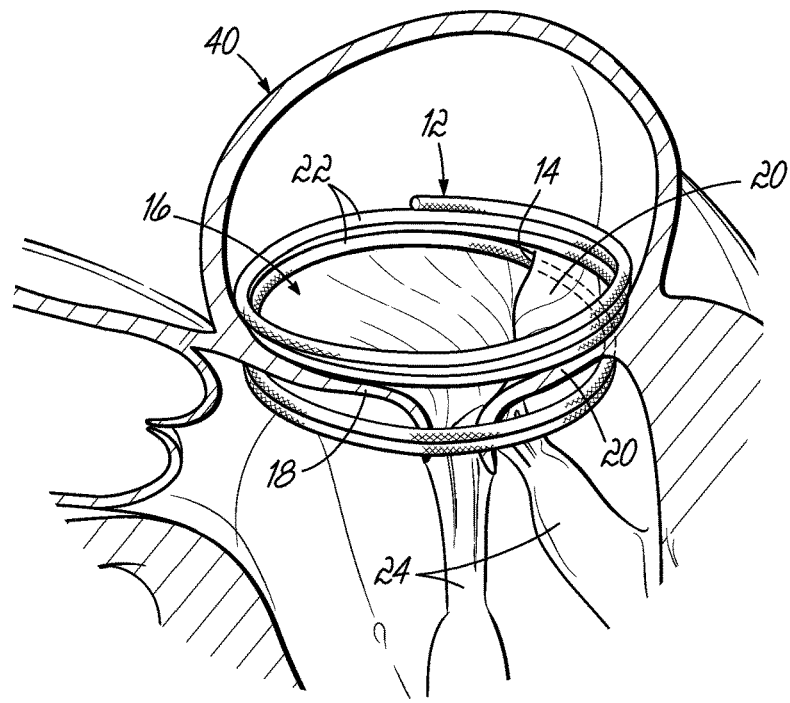
FIG. 8F is a perspective view showing the implanted helical anchor.
Figure 8G:
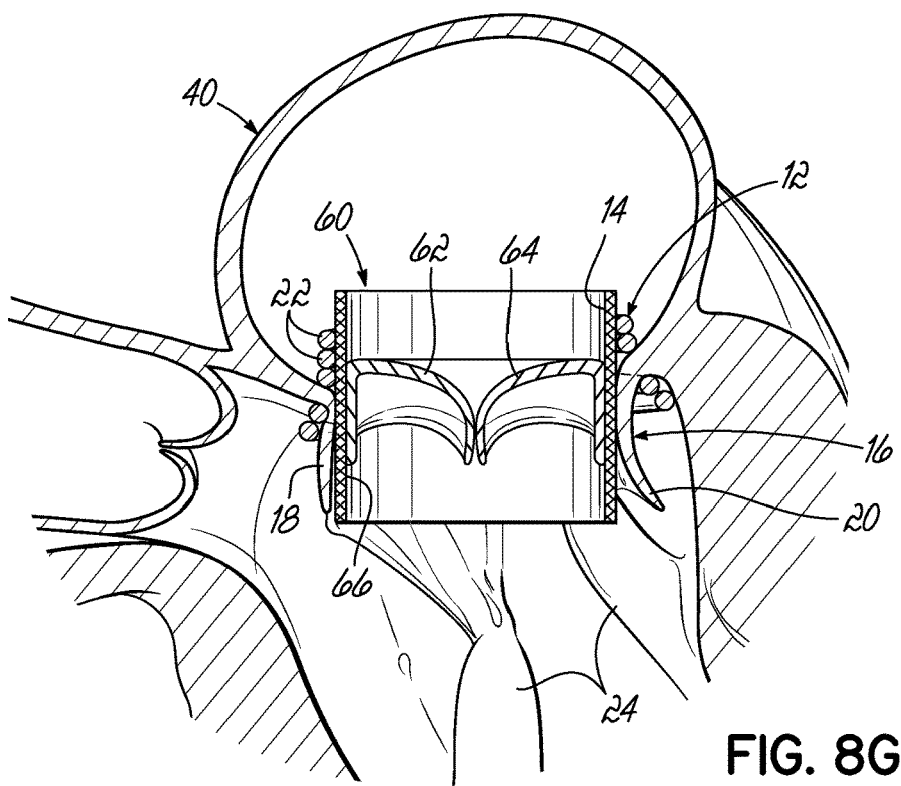
FIG. 8G is a cross-sectional view showing a replacement heart valve, such as a stent mounted valve, within the implanted helical anchor.

A procedure will now be described for introducing or implanting a helical anchor 12 in connection with FIGS. 6A, 6B, 7A, 7B, and 8A through 8C. A helical delivery tool 30 including coils 31 is used to deliver the helical anchor 12 which is contained within an outer tube 32, for example, formed from a Goretex or other low friction material, such as PTFE. Suture 34 is used to secure the combination or assembly of the outer tube 32 and helical anchor 12 in place on the coils 31 of the helical delivery tool 30. A groove (not shown) may be formed in the helical tool 30 so that it provides a secure seat for the suture. Additional suture 36 is used to tie the leading end of the outer tube 32 through a loop 38 at the end of the helical delivery tool 30. The helical delivery tool 30 and outer tube/helical anchor combination 32, 12 is turned into the heart 40, through the mitral valve 16 as shown and the suture 34 is cut, for example, with a scalpel 42 (FIG. 8B). A pair of forceps 44 is used to turn the tool 30 in through the native mitral valve 16 slightly more and this breaks the suture 36 (FIG. 8C). The helical tool 30 is then rotated in an opposite direction and removed from the heart 40, leaving the helical anchor 12 combined with the outer tube 32 in the heart 40, as shown. A push rod 50 with a cupped end 52 is inserted into the trailing end of the outer tube 32 (FIG. 8D). The outer tube 32 is then pulled backwards or rearward leaving the helical anchor 12 in place while removing the outer tube 32. Due to the low friction material of the outer tube 32, it easily slides off of the helical anchor 12. FIGS. 8F and 8G, respectively, show full implantation of this embodiment of the helical anchor 12 and a replacement heart valve 60 mounted within and firmly against the helical anchor 12. The replacement valve 60 includes leaflets 62, 64, and a body 66 which may be of any suitable design, such as an expandable stent design.

Figure 9:
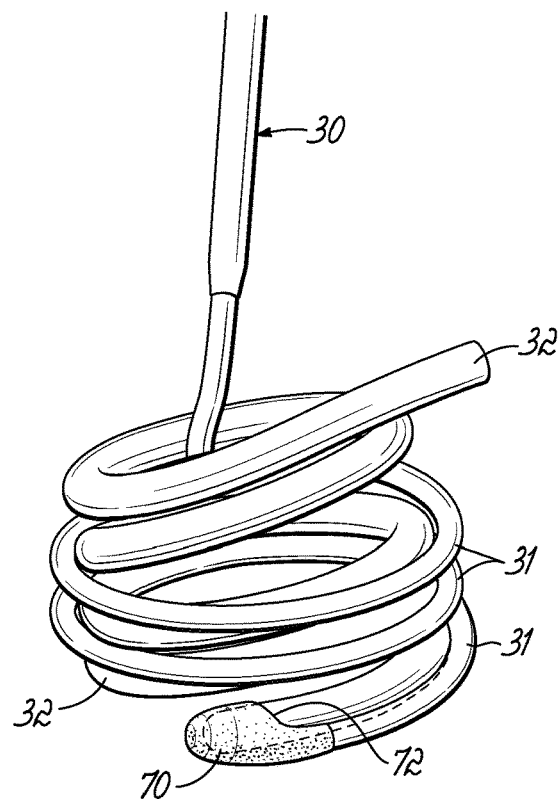
FIG. 9 is a perspective view illustrating another illustrative embodiment of a tool and assembly for implanting a helical anchor.
Figure 10:
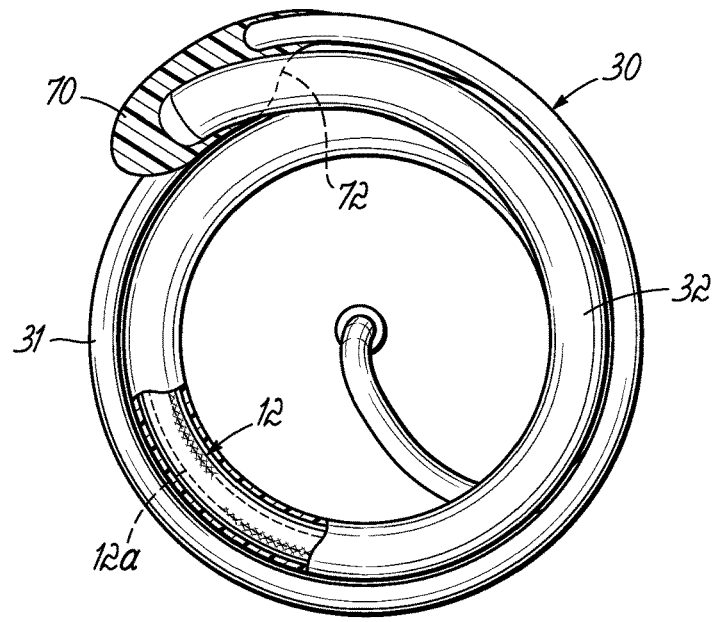
FIG. 10 is a partially cross-section top view showing the assembly of FIG. 9.

In another embodiment shown in FIGS. 9 and 10, a bullet shaped head 70 is provided on the helical tool 30. There is a slit 72 on the bullet-shaped head 70 that runs parallel to the helical shaped wire or coil 22 adjacent to the head 70. The bullet-shaped head 70 is formed from resilient, polymer, for example, and the slit 72 opens and closes by way of this resiliency. Again, the outer tube 32 is fixed to the helical delivery tool 30 with a suture (not shown). The leading end 32a of the outer tube 32 is inserted into the bullet-shaped head 70, for example, with forceps 44. In this embodiment, the bullet-shaped head 70 provides for easier insertion due to its tapered shape.

Figure 11A:
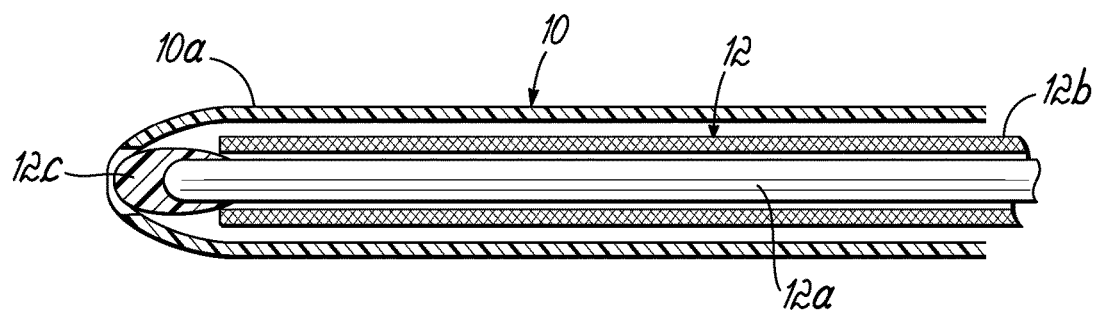
FIG. 11A is a cross-sectional view of the distal end of an alternative embodiment of a helical anchor and delivery catheter.
Figure 11B:
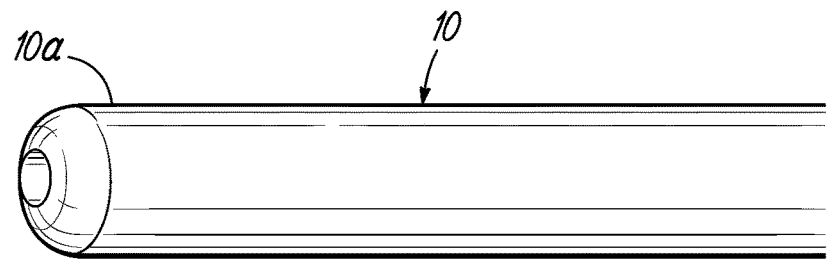
FIG. 11B is a perspective view of the distal end of another embodiment of a helical anchor and delivery catheter.

FIGS. 11A and 11B show additional illustrative embodiments of the combination of a delivery catheter 10 with a helical anchor 12 inside, before deployment. The distal tip 10a of the delivery catheter 10 includes a taper which may be gradually tapered as shown in FIG. 11A, or more rounded as shown in FIG. 11B. In each case, the distal tip 10a configuration allows for smoother, easier delivery to a native mitral valve location and can maneuver through tissue structure, such as native tissue, within the heart 40. For example, the distal end 10a of the delivery catheter 10 may be directed through the mitral valve 16 and may need to encircle the chordae 24 either partially or fully (FIG. 1). As shown in FIG. 11A, the helical anchor 12 may be constructed with an internal wire coil 12a and an external covering or coating 12b such as fabric, and may include a soft tip 12c, such as formed from polymer, to avoid damage to heart tissue during delivery and to enable easier delivery.

Figure 12:
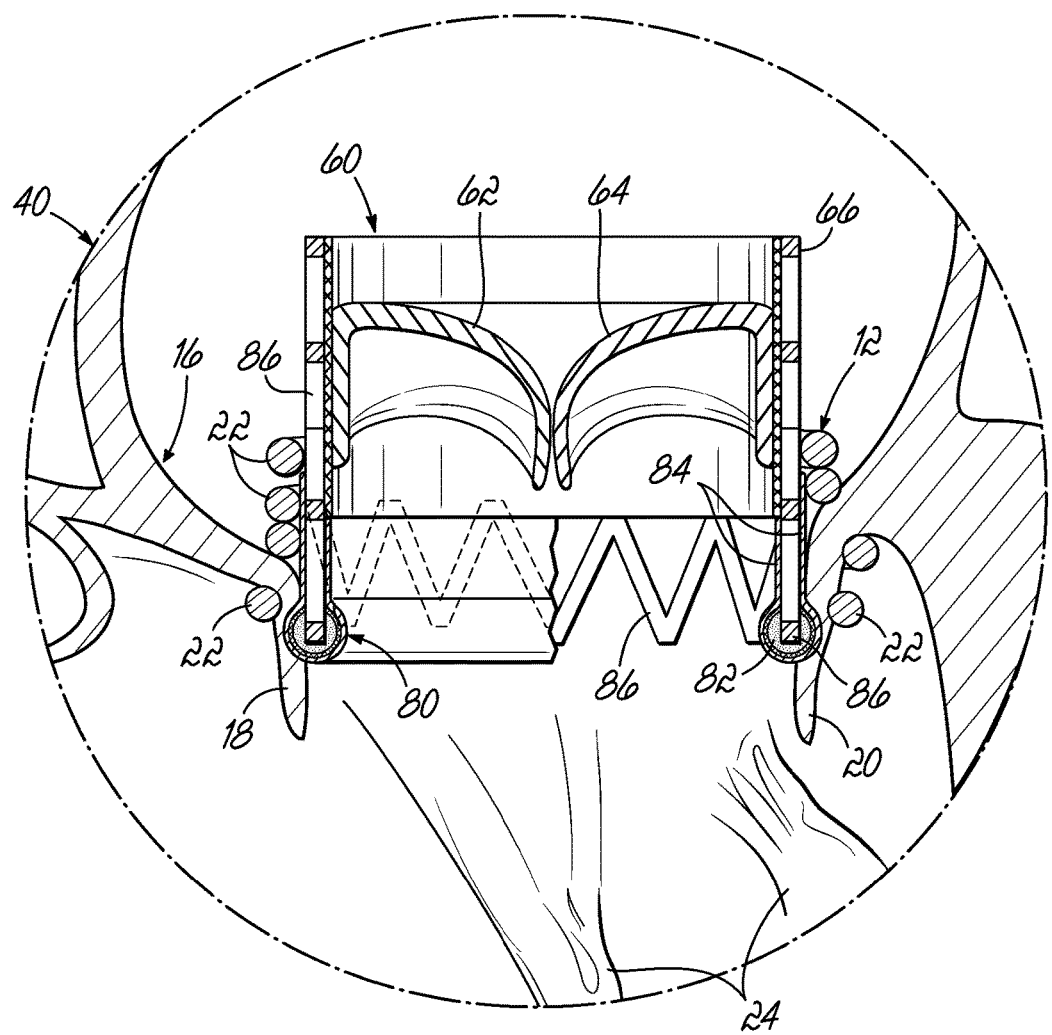
FIG. 12 is a cross-sectional view of an implanted replacement stent mounted valve and helical anchor at a native mitral valve location according to another illustrative embodiment.

FIG. 12 is a cross-sectional view showing an illustrative stent mounted replacement heart valve or prosthesis 60 at the native mitral valve 16 location docked in a helical anchor 12. In this embodiment, a "bumper" structure 80 has been added to the annular edge at the outflow end of the valve 60. This bumper structure 80 may be formed, for example, from foam 82 covered by a sealing material 84 such as fabric or another suitable material or coating. This sealing layer 84 extends upward over an open stent structure 86 of the valve 60 to prevent blood leakage past the valve 60 and through the coils 22 of the helical anchor 12.

Figure 13:
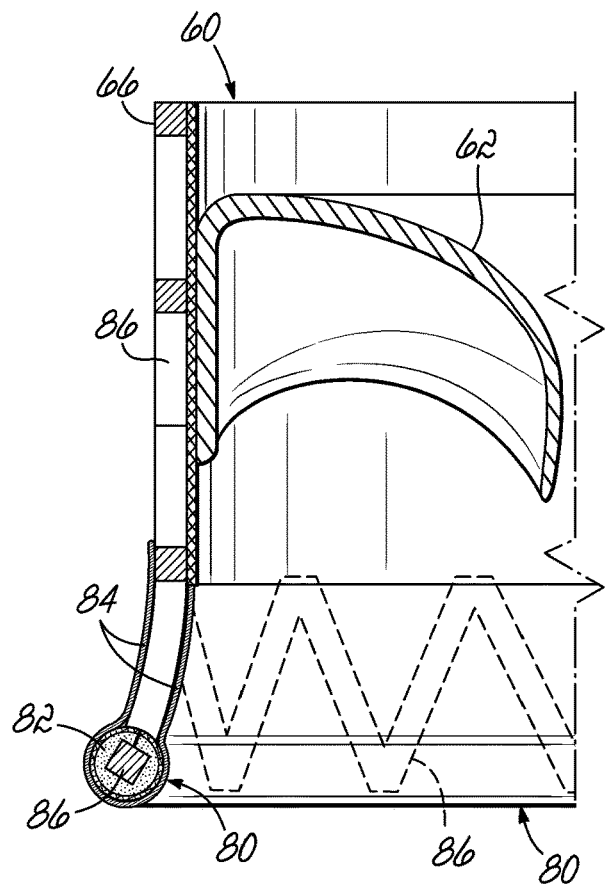
FIG. 13 is an enlarged cross-sectional view showing another illustrative embodiment of a stent mounted replacement heart valve.

FIG. 13 is an enlarged view of a replacement heart valve 60 similar to the valve shown in FIG. 12, but showing radially outward flared inflow and outflow ends.

Figure 13A:
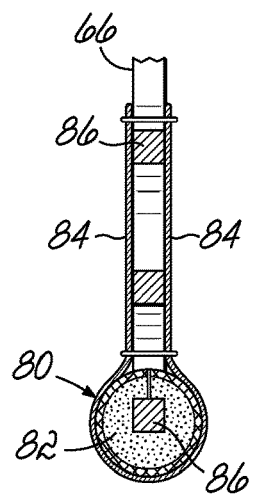
FIG. 13A is an enlarged cross-sectional view showing a non-flared embodiment of the outflow end of the replacement heart valve shown in FIG. 13.

FIG. 13A is an enlarged sectional view showing a generally cylindrical outflow end, without a radially outward flare.

Figure 14A:
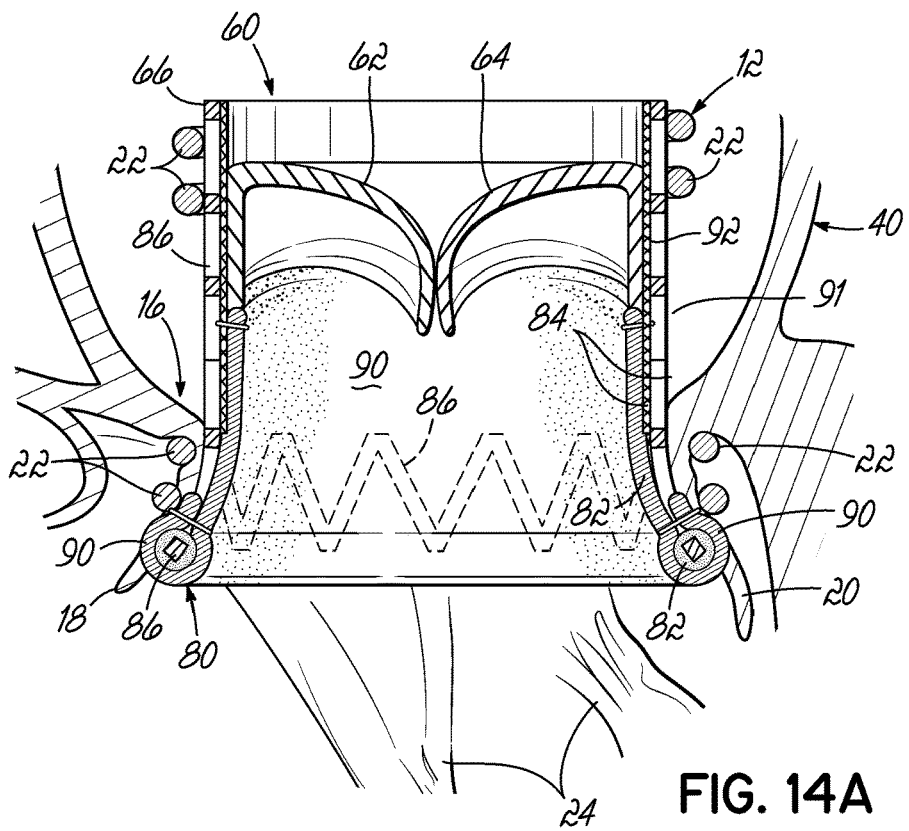
FIG. 14A is a cross-sectional view illustrating another illustrative embodiment of a replacement heart valve secured within a helical anchor.
Figure 14B:
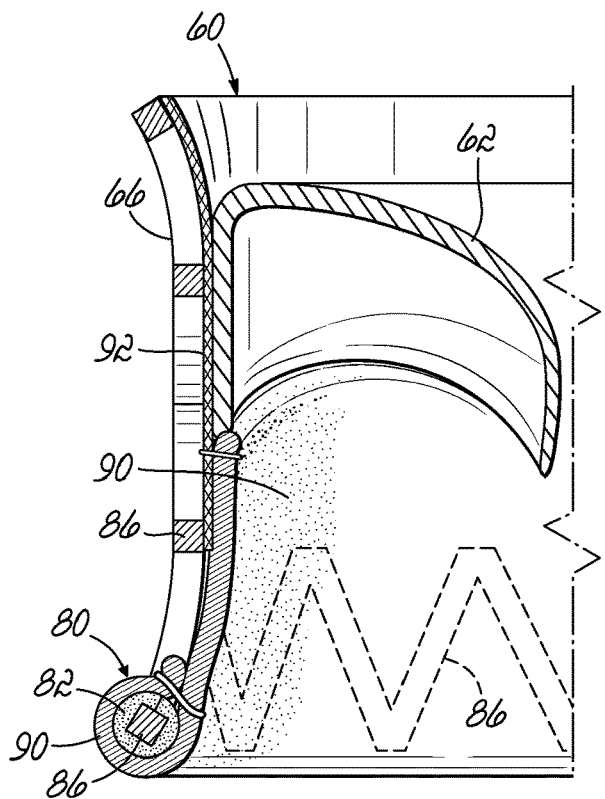
FIG. 14B is an enlarged cross-sectional view of the replacement valve shown in FIG. 14A.

FIGS. 14A and 14B illustrate another illustrative embodiment of the invention including a helical anchor 12 docking or mounting a replacement stent valve 60 and including biological tissue seal 90, such as pericardium tissue or other animal tissue used at both the location of the bumper 80 to cover the internal foam layer 82, as well as to seal and cover the open stent structure 86 up to the location of an existing fabric layer 92 circumscribing the replacement heart valve 60. The combination of the existing fabric layer 92 on the stent valve 60 and the seal layer 90 circumscribing the lower or outflow portion of the valve 60 prevents blood flow from leaking past the valve 60 through the stent structure 86. Instead, the blood passes as it should through the leaflets 62, 64 of the replacement valve 60. As further shown in FIG. 14A, the helical anchor 12 is preferably formed of spaced apart coils 22 creating a gap 91 such as configured in any embodiment previously discussed in connection with PCT Application Serial No. PCT/US2014/050525 the disclosure of which is hereby fully incorporated by reference herein, or spaced apart or formed as otherwise desired. As further described in PCT/US2014/050525, the helical anchor 12 is expansible by the stent valve 60.

Figure 15A:
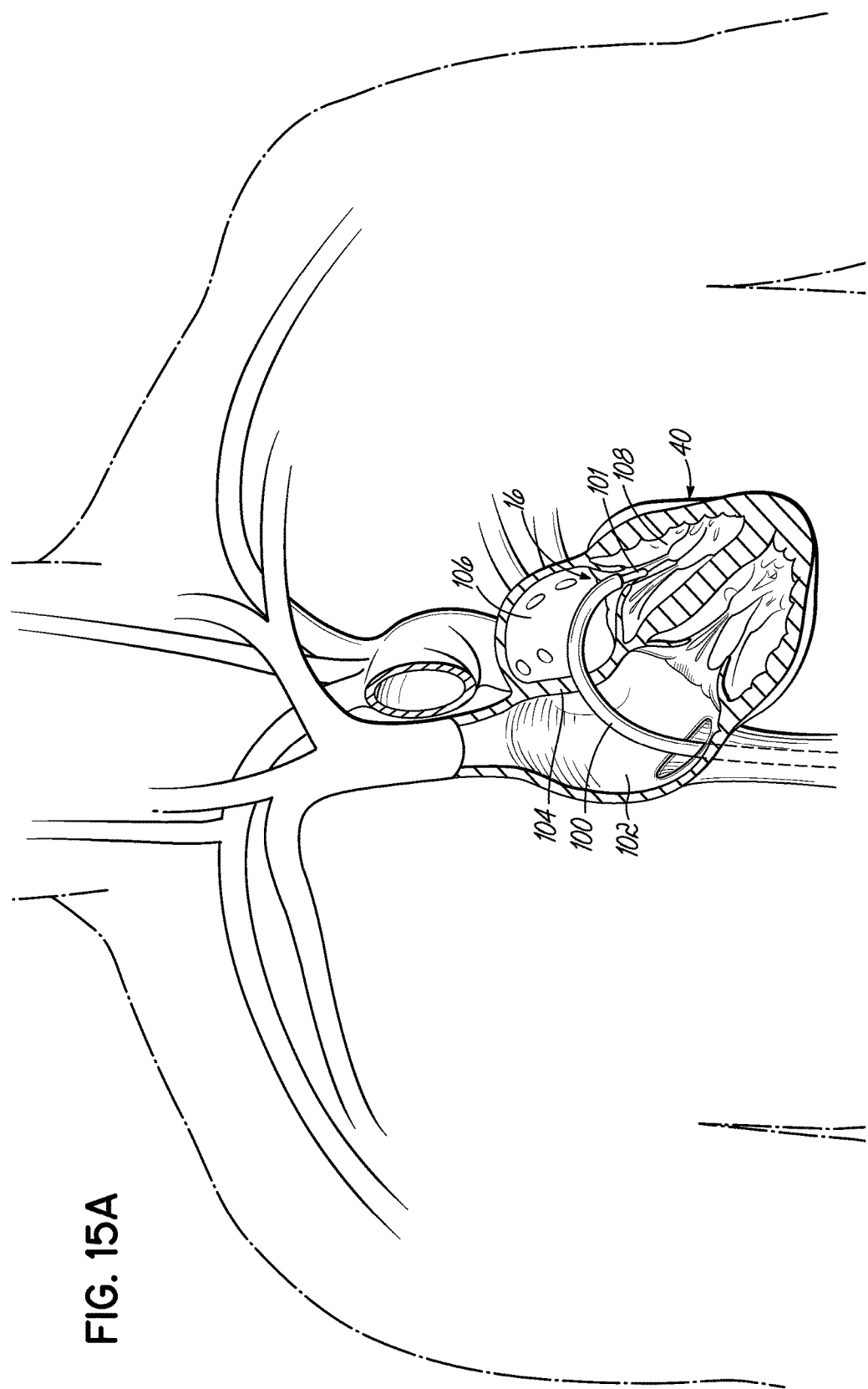
FIG. 15A is a schematic view showing a heart in cross section and initial introduction of a delivery catheter to the mitral valve location.
Figure 15B:
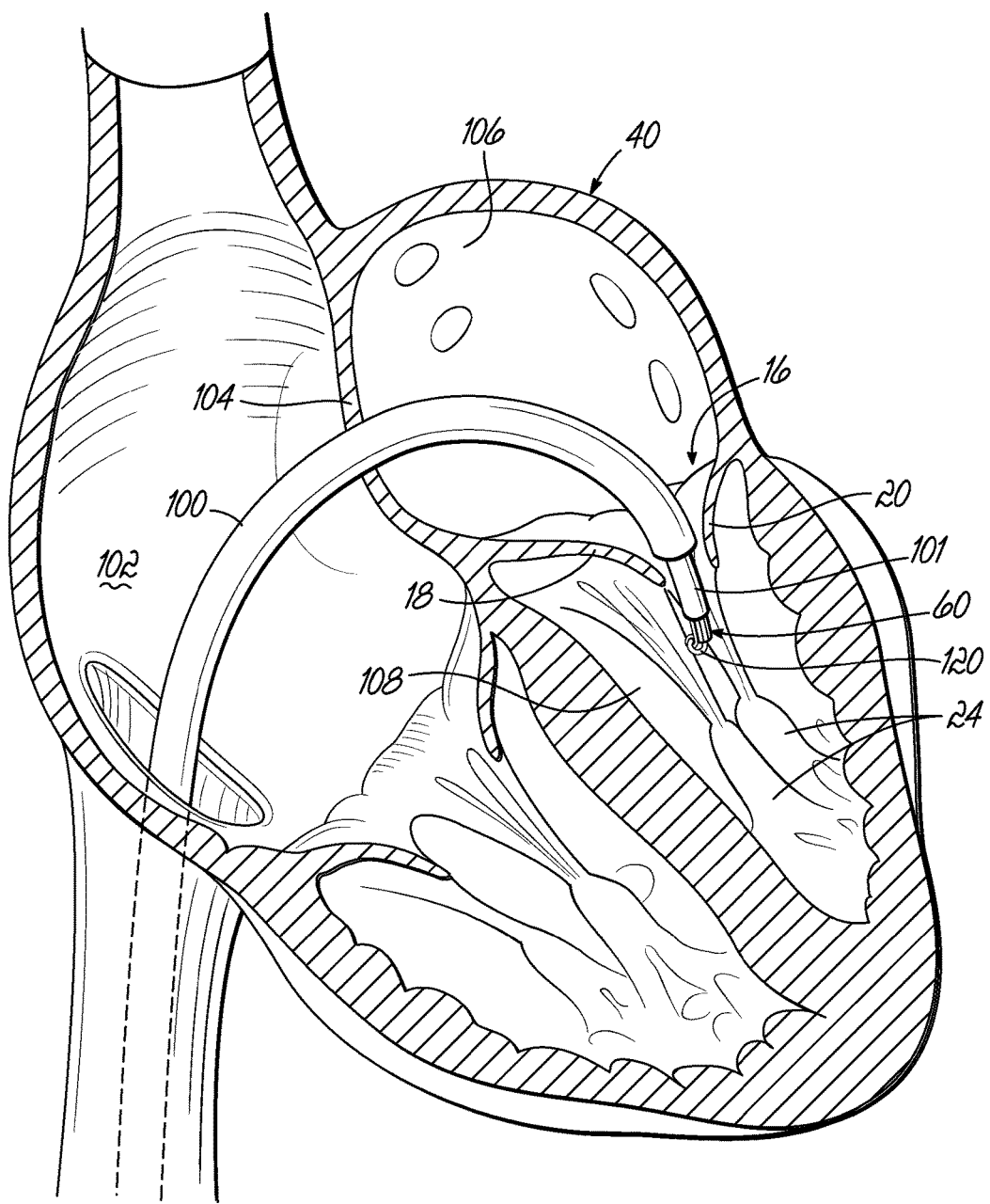
FIG. 15B is an enlarged cross-sectional view of the heart showing a further step in the introduction of a stent mounted replacement heart valve together with a helical anchor.
Figure 15C:
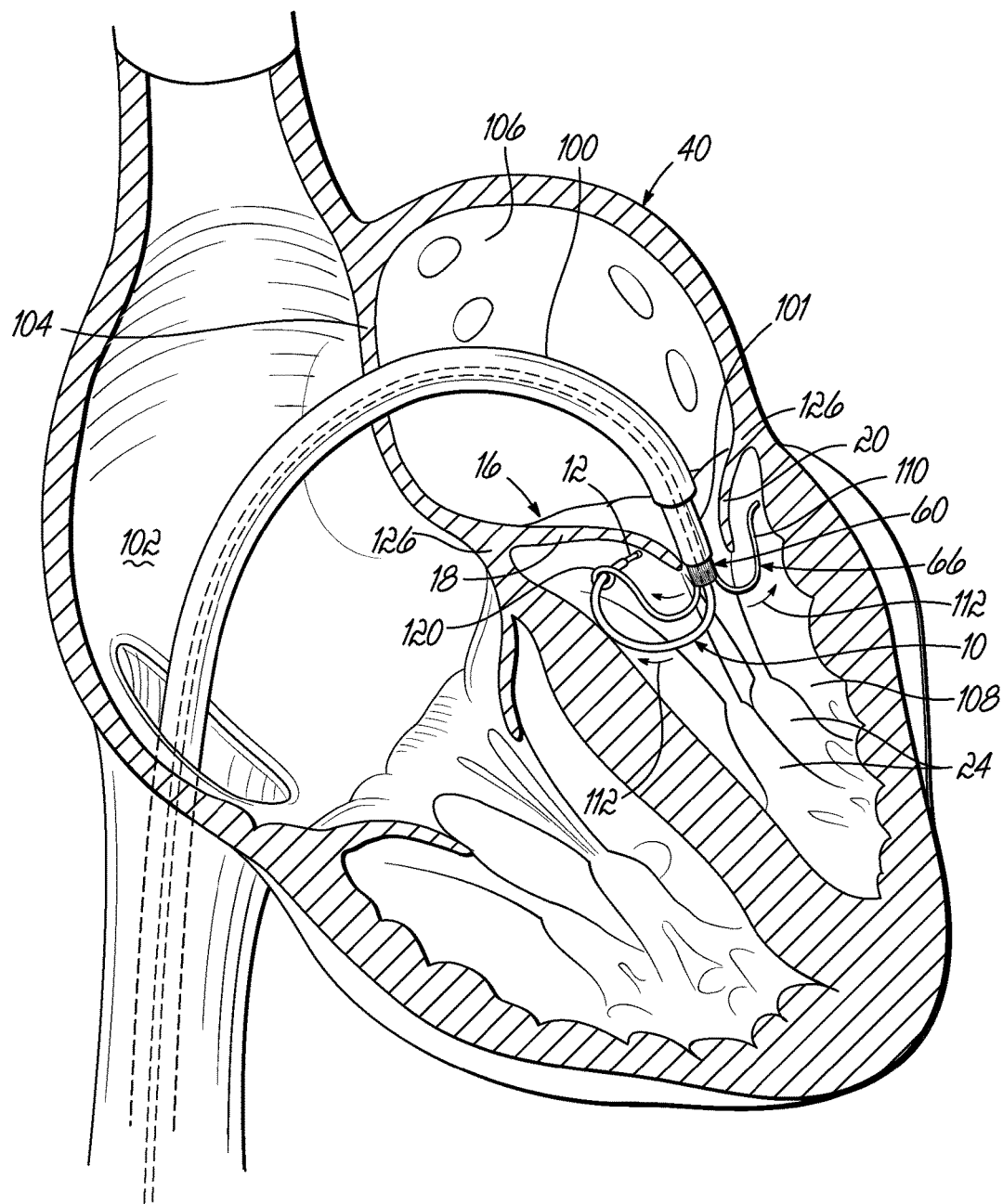
FIGS. 15C through 15F are views similar to FIG. 15B, but illustrating progressively further steps in the method of introducing the helical anchor and stent mounted replacement heart valve at the native mitral valve location.

Referring to FIGS. 15A-15C, an initial portion of a procedure according to another illustrative embodiment is shown. In this figure, a sheath 100 and delivery catheter 101 have been advanced through a peripheral vein into the right atrium 102 of the heart 40, across the atrial septum 104, to the left atrium 106. A distal end 10a of the delivery catheter 101 is positioned in the left ventricle 108 by being directed through the native mitral valve 16. This delivery catheter 101 contains a self-expanding or stent mounted mitral prosthesis or replacement valve 60 that is to be implanted at the location of the native mitral valve 16. A super elastic or shape memory type material, such as Nitinol, is typically used to form the frame structure or body 66 of the self-expanding replacement valve 60, but other materials may be used instead. The frame or body 66 includes artificial valve leaflets 18, 20 typically formed from tissue such as pericardial cow or pig tissue. Leaflets 18, 20 could instead be formed of other materials, such as synthetic or other biomaterials, e.g., materials derived from small intestinal mucosa. As described further below, the delivery catheter 101 also contains a helical anchor 12 and delivery system. The helical anchor 12 may generally take the forms described herein or previously disclosed, for example, in PCT Application Serial Nos. PCT/US2014/050525 and PCT/IB2013/000593. The disclosure of the PCT/IB2013/000593 application is also incorporated by reference herein.

FIG. 15B illustrates the delivery catheter 101 inside the left ventricle 108 with the distal tip 10a just below the native mitral valve leaflets 18, 20. The procedure has been initiated with exposure of the contents of the delivery system.

FIG. 15C illustrates another portion of the procedure subsequent to FIG. 15B and illustrating that the prosthetic or replacement mitral valve 60 has been partially delivered through the distal end 10a of the catheter 101. The end of the replacement valve 60 that is positioned in the left ventricle 108 has arms 110 that wrap around the native mitral leaflets 18, 20 and serve to anchor the replacement valve 60 firmly against the margins of the native mitral valve leaflets 18, 20. The arrows 112 show how the arms 110 have wrapped around the lower margins of the native mitral leaflets 18, 20 after the arms 110 have been extruded or deployed outwardly from the delivery catheter 101. This replacement valve 60 construction has been shown in the above-incorporated PCT Application Serial No. PCT/IB2013/000593. These arms 110 will help prevent the replacement valve 60 from dislodging upward into the left atrium 106 when the replacement valve 60 is fully positioned, because the arms 110 hook around the edges of the native mitral leaflets 18, 20. Multiple arms 110 are useful to provide a lower plane of attachment of the mitral valve prosthesis 60 to the native mitral valve 16. The arms 110 may vary in length and in character and construction. It will be understood that a plurality of arms 110 is used with this embodiment, but only two arms 110 are shown in these figures for purposes of illustration and simplification. One of the arms 110 includes a loop 120 to direct or control the helical anchor delivery catheter 10 that contains a helical anchor 12. The anchor delivery catheter 10 has been preloaded into the loop 120 before the assembly was loaded into the delivery sheath 100. The arm with the loop 120 may be of heavier construction than the other arms 110 and does not have to resemble the other arms 110. The arms 110 have shape memory property such that when they are extruded or deployed outwardly from the anchor catheter 10 they wrap around the native mitral leaflets 18, 20. The arm 110 with the loop 120 wraps around the native mitral leaflets 18, 20 and the attached helical anchor delivery catheter 10 is carried with it so that the chordae 24 and the native mitral valve leaflets 18, 20 are positioned inside the exposed end of the helical anchor 12.

When the helical anchor 12 is advanced or extruded as is initially shown in FIG. 15C, it will encircle the chordae tendinae 24 so that all valve and chordae will be trapped inside the helical anchor 12. The loop 120 swings the helical anchor delivery catheter 10 around the native mitral leaflets 18, 20 and above the chordae 24 into a preferred position under the native mitral valve annulus 126. The arm 110 with the loop 120 may have a dual function of attachment of the valve 60 to the native leaflet margin and for guidance during delivery of the helical anchor 12. The loop 120 may be sufficiently large to allow the helical anchor delivery catheter 10 to pivot or swivel as the system is deployed. It is important for the helical anchor 12 to be extruded in a plane close to parallel to the underside of the native mitral valve 16. The helical anchor delivery catheter 10 is also aimed or oriented to this plane by the loop 120. The loop 120 may, in fact, be composed of a short tube (not shown) instead of a wire as shown. A tube would force the helical anchor delivery catheter 10 into a favorable plane and orientation. Alternatively, the helical anchor delivery catheter 10 could be steerable in one of the manners known through steerable catheter technology.

Other mitral valve prosthesis or replacement valves may be used and have a wide range of attachment arms or wings, or stent structure, that wrap around the native mitral valve leaflets 18, 20. The arms or other similar structures in such prostheses could all be fitted with a loop 120, or tube or other similar guidance structure, to perform similar functions as the loop 120 described immediately above. This function generally relates to directing the delivery of the helical anchor 12. Furthermore, it is not necessary that a loop 120 directs the helical anchor delivery. For example, a cell or opening of the replacement valve stent structure 86 could also perform the same function as the loop 120 shown and described in these figures. A hook or a tube may also be used in lieu of the illustrated loop 120. Any structure that can function to direct the helical anchor 12 around the native mitral valve leaflets 18, 20 may be added to the prosthetic or replacement heart valve 60. The structure may be permanently fabricated as part of the replacement valve 60 or may be temporary structure used only during the procedure. For example, a loop of suture (not shown) may be used to guide delivery of a helical anchor 12 including any helical anchor delivery catheter 10 associated therewith. After use of the suture, it may be withdrawn from the patient.

The arms 110 illustrated in these figures are quite narrow or slender. In practice, it may be more useful to have arms that are composed of pairs or triplets of wires that are fused at the ends. The narrow terminal ends of the arms 110 facilitate the arms 110 passing between the chordae tendinae 24 at their margins with the free edge of the native mitral leaflets 18, 20 to allow the arms 110 to wrap around the native leaflets 18, 20. The chordae 24 are closely packed in some areas and slender arms 110 will allow the arms 110 to pass between the chordae tendinae 24. Once the slender portion of the arms 110 pass, thicker portions of the arms 110 may move between the chordae 24 by spreading them apart. Therefore, an arm 110 that is slender or composed of a single wire or fusion of wires at the tip and that is more robust or thicker closer to the main body of the prosthetic or replacement valve 60, may be a desirable arrangement. The wires or arms 110 may also be much shorter than those shown in these illustrative figures. In the illustrated method, delivery of the helical anchor 12 may be started at any desired location and not necessarily at the commissure 14 of the native mitral valve 16. For example, delivery may start in the middle portion of a native mitral leaflet 18 or 20. This would be advantageous for the surgeon who would not have to precisely locate the commissure 14 to begin the procedure, thereby greatly simplifying the procedure.

Figure 15D:
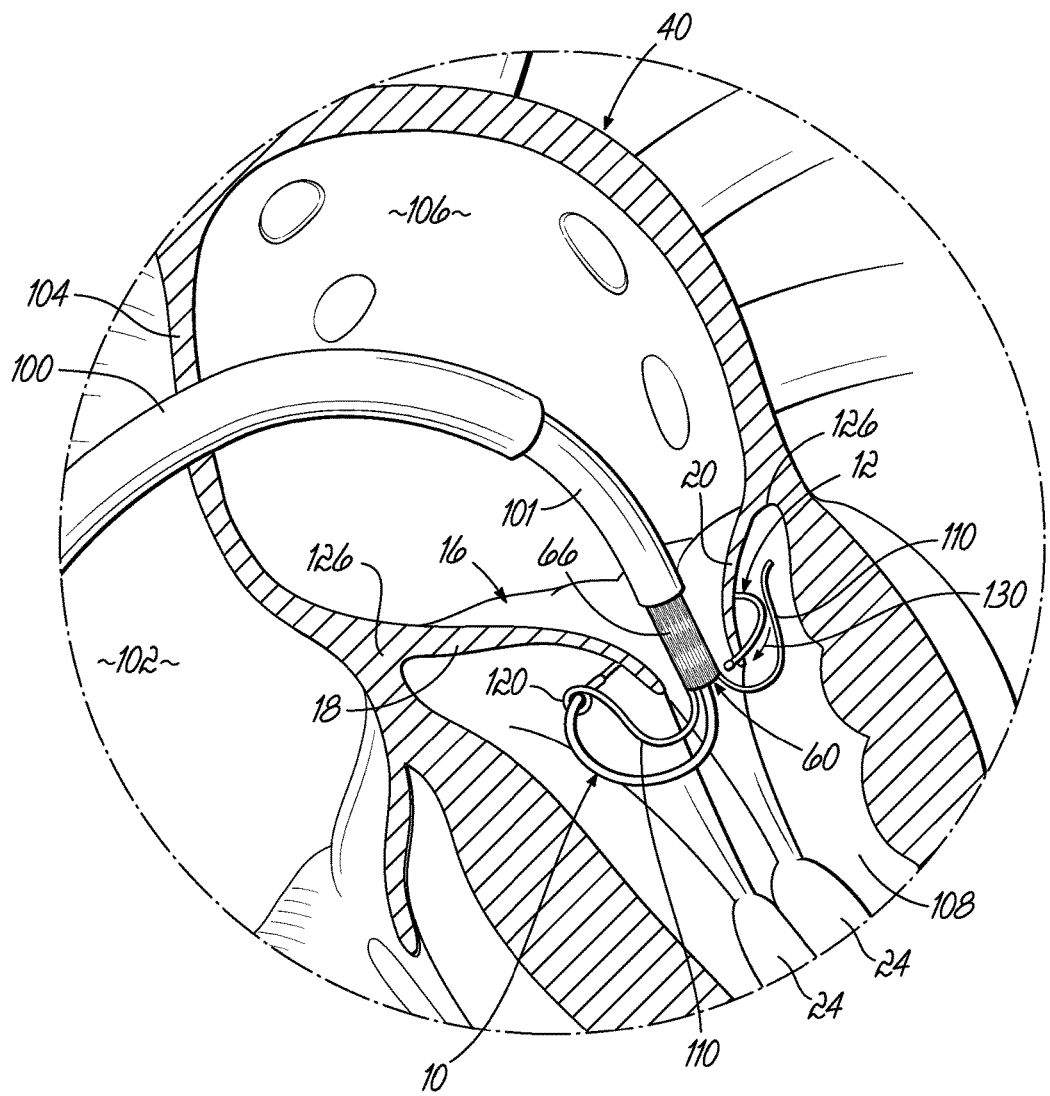

FIG. 15D illustrates the helical anchor 12 being delivered under the native mitral leaflets 18, 20. The arrow 130 indicates the helical anchor 12 being extruded from the helical anchor delivery catheter 10 under the native mitral valve 16. Any number of coils or turns 22 of the helical anchor 12 may be extruded depending on the particular configuration of helical anchor 12 being used in the procedure. The inner diameter of the helical anchor 12 would preferentially be slightly less than the outer diameter of the fully expanded mitral valve prosthesis 60 to promote firm engagement or anchoring of the replacement mitral valve 60. The helical anchor 12 may be composed of bare wire, or may have coatings or coverings for various reasons such as those described in the above incorporated PCT applications. The partially delivered mitral valve prosthesis 60 serves an important function to center the delivery of the helical anchor 12. The mitral valve prosthesis or replacement valve 60 also provides a stable platform.

Figure 15E:
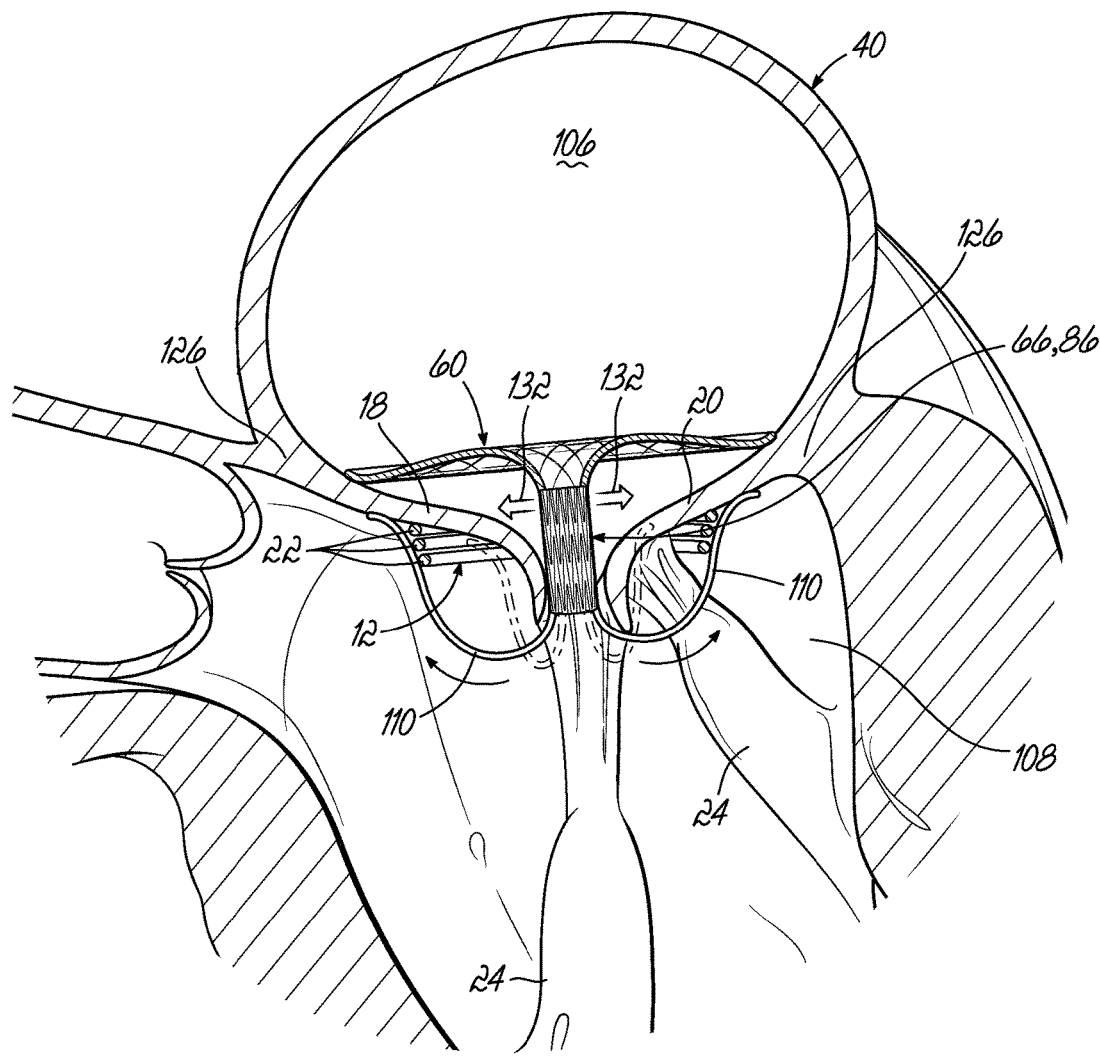

FIG. 15E illustrates that three turns 22 of the helical anchor 12 have been placed below the native mitral valve 16. These turns or coils 22 have positioned the native mitral valve leaflets 18, 20 between the helical anchor 12 and the prosthetic mitral valve 60 which is shown in a configuration about to be expanded. Once the replacement valve 60 is expanded, this securely positions the replacement valve 60 and prevents leaks around the replacement valve 60 by sealing the native mitral leaflets 18, 20 to the prosthesis 60. The delivery sheath 101 for the replacement valve 60 has been removed and when using a self-expanding valve, the valve 60 would spring open upon removal of the delivery sheath 101. The arrows 132 indicate this process prior to its occurrence. In this figure, the replacement valve 60 is still in a closed position to allow clear visualization of the turns or coils 22 of the helical anchor 12 beneath the native mitral valve 16. In this configuration, there are three helical anchor coils 22 below the native mitral valve 16, however, any number of coils 22 may be used instead. The coils 22 are positioned up against the underside of the mitral valve annulus 126 and leaflets 18, 20 to provide a solid buttress to fix the helical anchor 12 in position and prevent movement into the left atrium 106 when the powerful left ventricle 108 contracts. When the arms 110 wrap around the helical anchor 12, the entire structure or assembly is stabilized in position. This embodiment provides a surgeon or interventionalist a considerable amount of choice due to the fact that the anchor 12 may be delivered at the same time as the replacement valve 60. Many shape memory framed prosthetic heart valves 60 may be re-sheathed. This means that during a procedure, the replacement valve 60 may be partially advanced from a catheter or sheath 101 and tested for its fit in the heart 40. If the surgeon or interventionalist is not satisfied with the positioning of the replacement valve 60 before the final release of the replacement valve 60, this valve 60 may be pulled back into the sheath or catheter 101. Therefore, a prosthetic or replacement valve 60 may be positioned initially with no helical anchor 12 in place. If subsequent anchoring appeared strong and stable and there was no evidence of movement or leakage, the valve 60 may be released. On the other hand, if the surgeon or interventionalist is not satisfied, the valve 60 may be pulled back into the sheath 101. The helical anchor 12 may be implanted first, and then the valve 60 may be extruded from the delivery sheath 101. This would allow the user to decide on the clinical need for additional anchoring under the native mitral valve 16.

Figure 15F:
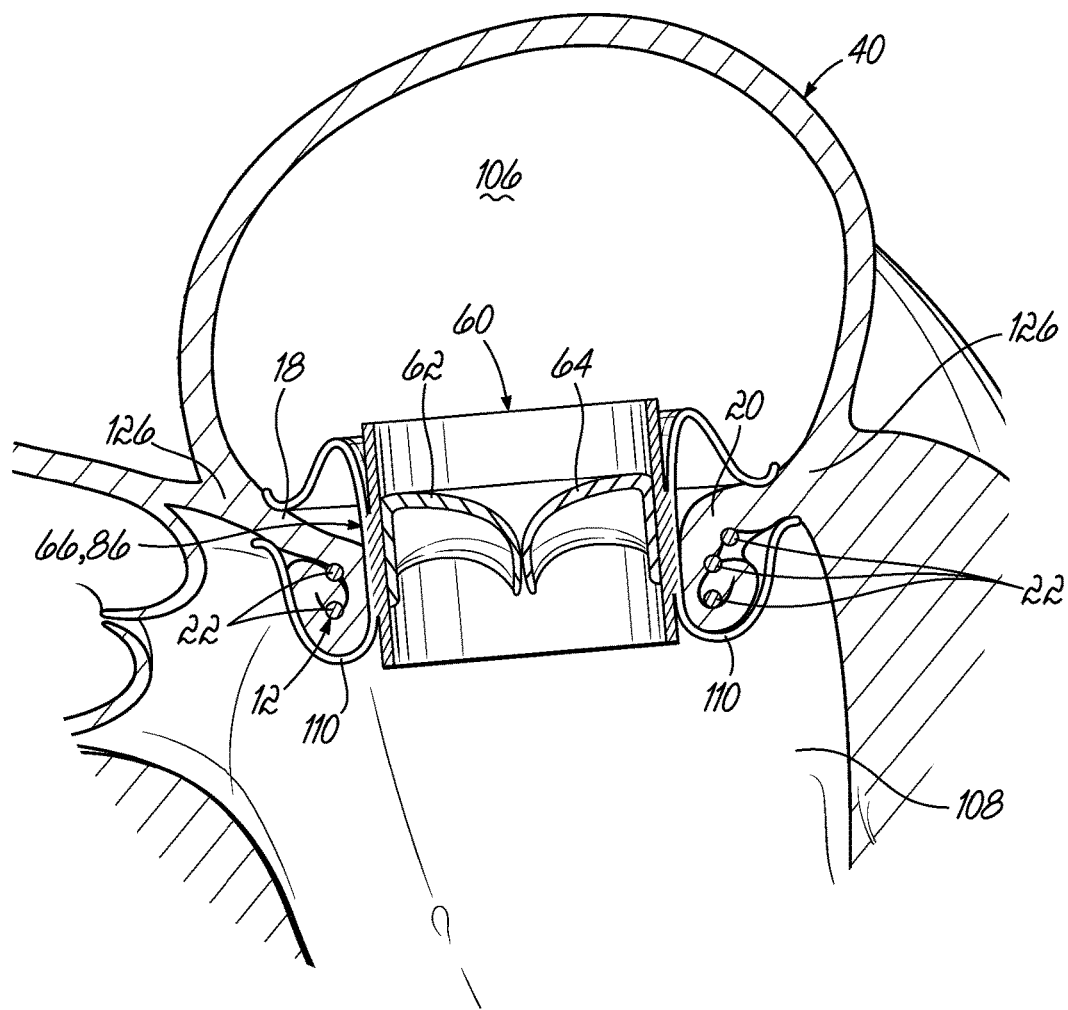

FIG. 15F illustrates the fully implanted expandable replacement valve 60 shown in proper position. The arms 110 have wrapped around the native mitral valve leaflets 18, 20 to prevent the replacement valve 60 from moving upward into the left atrium 106. The native mitral leaflets 18, 20 are compressed under the arms 110 and a very solid mechanical structure and anchoring has been created to prevent the replacement valve 60 from migrating to an undesirable position. The turns or coils 22 of the helical anchor 12 also compress against the body 66 of the prosthetic or replacement valve 60 to position, orient and prevent movement of the replacement valve 60. Therefore, the helical anchor 12 provides a friction attachment of the replacement valve 60 and serves to anchor the arms 110 that wrap around the helical anchor 12. The upper portion of the native mitral valve 16 is shown with a wider area that sits inside the left atrium 106 to promote attachment to the wall of the left atrium 106. However, the force moving the replacement valve 60 from the left atrium 106 toward the left ventricle 108 is low and this portion of the replacement valve 60 may not be necessary and could be eliminated or reduced from a clinical prosthesis. The turns or coils 22 of the helical anchor 12 are important because they can overcome a wide variety of variations in the lengths of the native mitral leaflets 18, 20 from patient to patient and the length of the chordae tendinae 24 and the attachment points of the chordae 24 in the left ventricle 108. When a replacement valve 60 with arms 110 wrapping around the native mitral leaflets 18, 20 is used without any helical anchor 12 encircling under the native leaflets 18, 20, the depth of fixation of the prosthetic mitral valve 60 may vary around the perimeter of the implanted replacement valve 60. For example, if the chordae tendinae 24 attached to the middle part of the posterior leaflet 20 were very elongated or ruptured, which is a common situation, the arms 110 may fail to wrap around and engage the native leaflet 20 at this location. Alternatively, there may be a very limited engagement along or at a much higher plane. This portion of the replacement valve 60 would be positioned higher, creating a skew in the replacement valve 60 so that the replacement valve 60 would be positioned at an angle to the plane of inflowing blood through the replacement valve 60. As the heart 40 beats, there is a large load on the replacement valve 60 and it may begin to rock and shift. The heart 40 beats almost 100,000 times per day and after several days or weeks or months, the valve 60 may shift, move and/or dislodge. Also, if the leaflets 18, 20 and/or chordae 24 were very elongated, there may be no contact with the arms 110. This could result in a large perivalvular leak due to lack of engagement of the replacement valve 60 with the native mitral leaflets 18, 20. An anchor 12 under the native mitral valve leaflets 18, 20 would compress native leaflet tissue against the replacement valve 60 and prevent this problem. The helical anchor 12 would be positioned in one plane and prevent problems related to variations in patient anatomy.

In clinical practice, there are virtually limitless variations in the size of the native mitral leaflets 18, 20, character of the native mitral leaflets 18, 20, the chordal lengths and the attachment of the chordae 24 as well as the diameter of the mitral annulus 126. The use of a helical anchor 12 or other anchor structure under the native leaflets 18, 20 neutralizes many of these variables since the fixation point of the arms 110 may be brought to the lowest coil 22 of the helical anchor 12. This position may also be determined in advance by selecting the number of coils 22 in the helical anchor 12 as well as the thickness of the coils 22 in the helical anchor 12 to match the turning point of the arms 110 on the lowest portion of the replacement valve 60. Thus, an important feature of the helical anchor 12 delivered under the native mitral annulus 126 is that it can create a common and predefined plane for anchoring the arms 110 of the replacement valve 60. In the situation described above in which some of the chordae 24 are stretched, the attachment in this region of the replacement valve 60 could be to the helical anchor 12. This would create a common plane for the lowest point on the replacement valve 60. To ensure that the valve 60 anchors at a common lowest plane throughout its perimeter, additional coils 22 may be added to the helical anchor 12, or the diameter of the coils 22 may be made larger. Additional options are, for example, waves or undulations may be added to the coils 22 of the helical anchor 12 to expand the overall height of the helical anchor 12. The helical anchor 12 therefore improves stability of the replacement valve 60 by providing an anchoring point or location for the arms of the replacement valve 60 to wrap around while, at the same time, the helical anchor 12 can trap the perimeter of the replacement valve 60 along its length. The combination of these features provides for increased stability to the replacement valve 60 and can also seal the replacement valve 60 against the native mitral valve 16 to prevent perivalvular leakage of blood flow. As mentioned, the native mitral valve and heart structure of patients comes in many varieties and combinations. It is not practical for a manufacturer to make different lengths and depths of anchoring arms 110 and for the user to deliver these products optimally into position for each case. Rather, it is much more practical to adjust for these variations by placing a helical anchor 12 below the native mitral valve 16 and using this to create a lowest plane for the arms 110 to anchor against. The delivery system for the helical anchor 12 may be any delivery or deployment system, for example, described in the above-incorporated PCT applications. It will be appreciated that such deployment methods and apparatus may be used to deliver the helical anchor 12 such that the anchor 12 is positioned only below the native mitral valve 16 as shown herein.

Figure 16A:
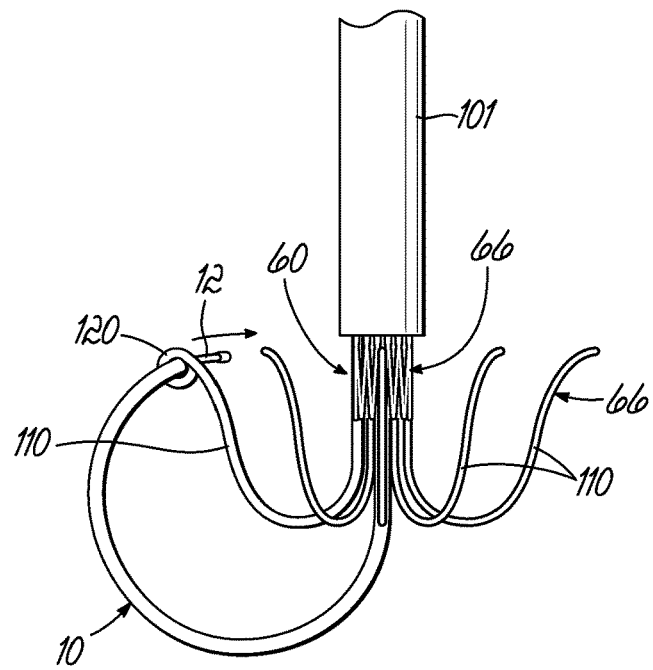
FIGS. 16A and 16B are schematic elevational views showing the simultaneous deployment of a stent mounted replacement heart valve and a helical anchor using an arm with a loop on the stent valve.
Figure 16B:
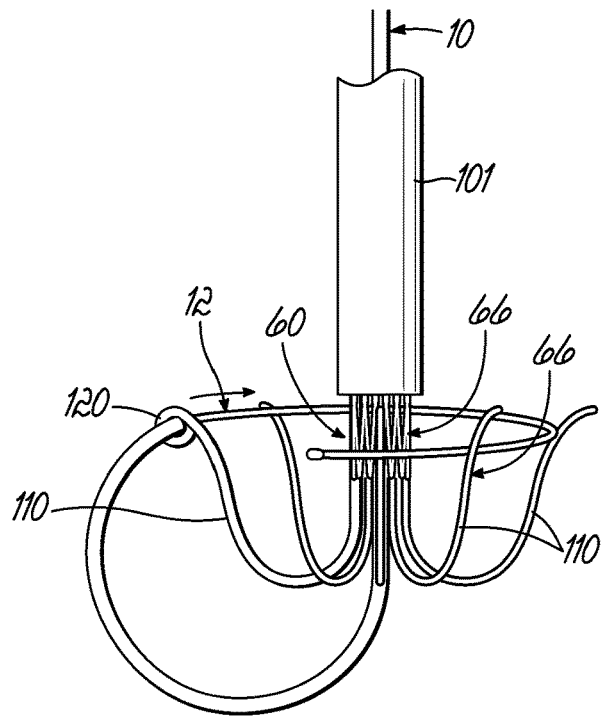

FIGS. 16A and 16B illustrate another embodiment in which a loop 120 is provided at the end of an arm 110 on the replacement valve 60 that guides the helical anchor delivery catheter 10. This loop 120 allows the delivery catheter 10 to swivel as it is moved into position. In this embodiment, the helical anchor delivery catheter 10 passes through the replacement valve 60 or, in other words, within the replacement valve body 66, however, it may be directed in manners other than that shown, and the helical anchor delivery catheter 10 may be used for additional guidance along the path, such as by being steerable after being directed through the loop 120 farther than as shown in FIGS. 16A and 16B for delivery of the helical anchor 12.

Figure 17A:
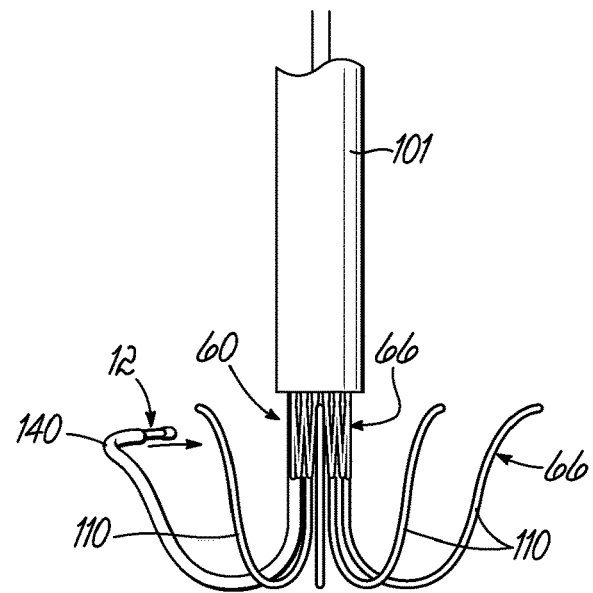
FIGS. 17A and 17B are similar to FIGS. 16A and 16B, but illustrate another embodiment.
Figure 17B:
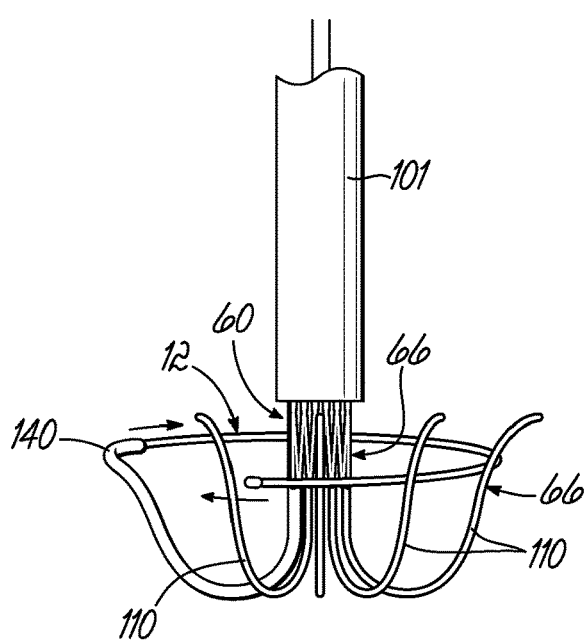

FIGS. 17A and 17B illustrate another embodiment in which a helical anchor delivery tube 140 has been incorporated into the replacement valve 60 instead of the helical anchor delivery catheter 10 previously described. In this embodiment, one arm of the replacement valve 60 is, in fact, the tube 140 that is loaded with and carries the helical anchor 12. When the tubular arm 140 wraps around the native mitral valve leaflet (not shown), the helical anchor 12 is carried into the correct location and to the correct plane for delivery. Any structure on one of the arms 110 of the replacement valve 60 or any portion of the replacement valve 60 that may guide the helical anchor 12 for delivery may be used instead. In FIG. 17B, the helical anchor 12 has been extruded from the tubular arm 140 for almost one complete rotation or turn. As previously described, multiple turns or coils 22 of the helical anchor 12 may be deployed in this manner for ultimately securing the replacement valve 60 at the native mitral valve 16 location generally as described above. The main difference with this embodiment is that a helical anchor delivery catheter 10 is not needed.

FIGS. 18A through 18C illustrate another embodiment for replacement valve and helical anchor deployment and implantation. In this regard, the helical anchor delivery catheter 10 and the replacement valve 60 are essentially delivered side by side. FIG. 18A illustrates the helical anchor delivery catheter 10 outside or extruded from the delivery sheath 101 that also delivers the replacement valve 60. The helical anchor delivery catheter 10 passes through a loop 120 in one of the arms 110 of the replacement valve 60. The arrow 150 indicates that the helical anchor 12 is about to be extruded from the end of the helical anchor delivery catheter 10. As shown in FIG. 18B, with the end of the helical anchor delivery catheter 10 still in the loop 120, almost one full turn or coil 22 of the helical anchor 12 has been delivered under the native mitral valve (not shown). FIG. 18C illustrates a further point during the implantation process in which about three turns or coils 22 of the helical anchor 12 have been delivered under the plane 152 of the native mitral valve 16. In this figure, the helical anchor delivery catheter 10 and the sheath 101 delivering the replacement valve 60 have been removed. When the replacement valve 60 is formed with a self-expanding stent, the body 66 of the valve 60 will spring open when the delivery sheath 101 is removed. For purposes of clarity and illustration, the valve 60 is still shown in a closed or unexpanded state simply for clarity. However, in general, the fully implanted system or assembly will be similar to that shown in FIG. 15F.

Figure 19A:
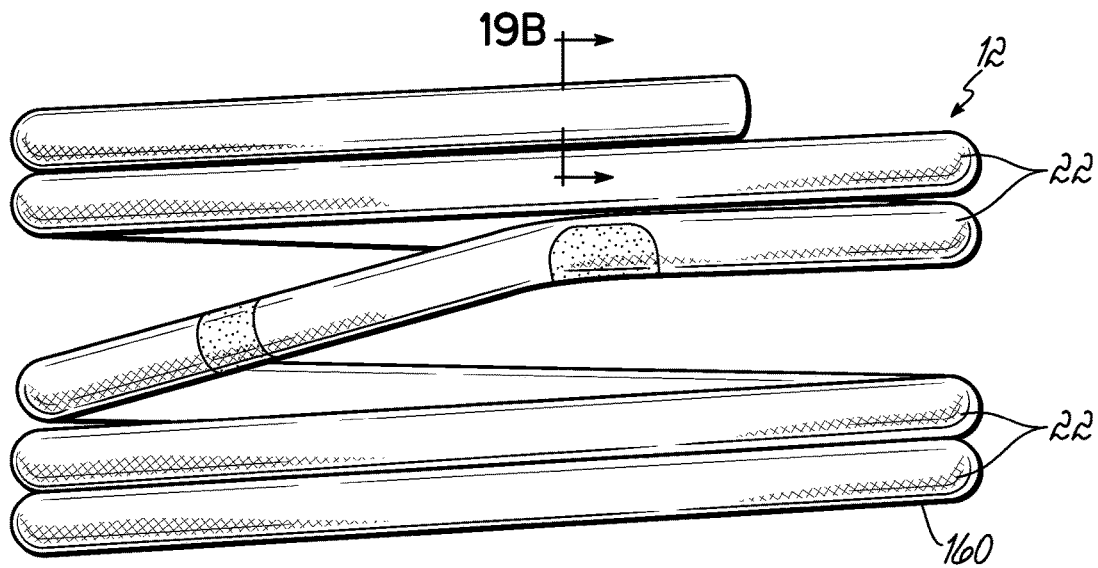
FIG. 19A is a side elevational view of a helical anchor constructed in accordance with another illustrative embodiment.
Figure 19B:
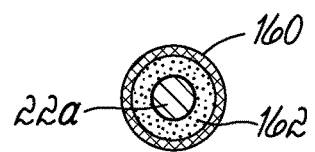
FIG. 19B is a cross-sectional view taken along line 19B-19B of FIG. 19A.

FIGS. 19A and 19B illustrate another embodiment of a helical anchor 12. In this embodiment, the configuration of the helical anchor 12 in terms of the spacings and size of the coils 22 may vary. The cross-sectional construction includes a fabric covering 160 which may, for example, be PET having a thickness of 0.008+/−0.002 inch, a weight of 2.12+/−0.18 ounce/yard$^2$ (72+/−6 grams/m$^2$), a wale/inch of 40+/−5, courses/inch of 90+/−10. A foam layer 162 may, for example, be 2 mm thick polyurethane sheet material. The foam may be attached to the fabric 160 using PTFE suture with a light straight stitch. The fabric 160 and foam 162 may then be folded around the center wire portion 22a of the coils 22 of the helical anchor 12 and cross-stitched to the wire portion 22a using fiber suture.

Figure 20:
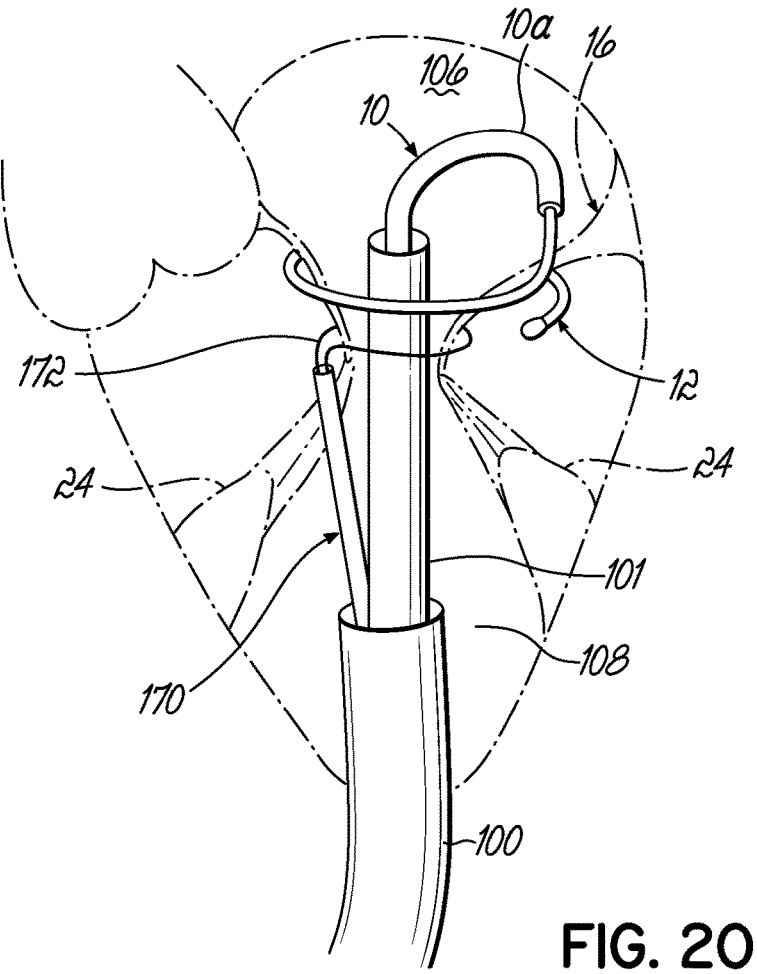
FIG. 20 is a schematic perspective view illustrating another alternative system for delivering a helical anchor.

FIG. 20 illustrates another system which may include the delivery of a helical anchor 12 as set forth above and/or in the above incorporated PCT applications. In accordance with this embodiment, however, an additional tissue gathering device 170 is included in the delivery system. The device 170 delivers a temporary ring or loop 172 which can corral or surround the bundles of chordae tendinae 24 into a smaller area. This can facilitate easier placement of the helical anchor 12 without entanglement or obstruction with the chordae tendinae 24. Also, shown in this figure is an introducer sheath 100, a delivery catheter 101 as well as a steerable helical anchor delivery catheter 10 all generally as previously described.

Figure 21A:
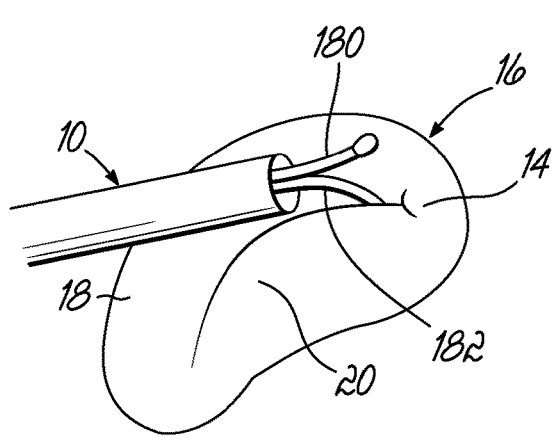
FIG. 21A is a schematic perspective view illustrating the initial delivery of an alternative helical anchor.
Figure 21B:
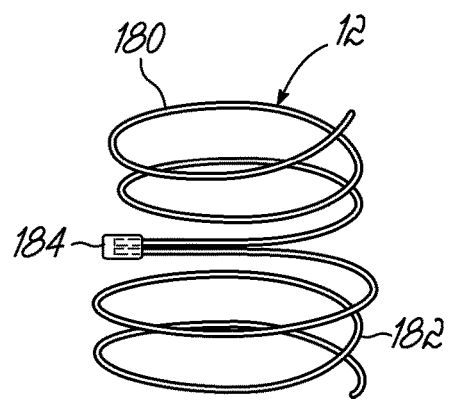
FIG. 21B is a schematic perspective view of the fully delivered helical anchor of FIG. 21A.

FIGS. 21A and 21B illustrate another helical anchor device or assembly 12. The assembly 12 is comprised of an upper or atrial helical anchor portion 180 as well as a lower or ventricular helical anchor portion 182. These helical anchor portions 180, 182 are delivered simultaneously by extruding out of a helical anchor delivery catheter 10. The lower anchor portion 182 is delivered through the mitral valve 16 between the native leaflets 18, 20. The upper and lower anchor portions 180, 182 may be coupled together, for example, by a crimp joint 184. The upper anchor portion 180 is deployed above the native mitral valve 16 in the left atrium 106 (FIG. 20). The upper and lower anchor portions 180, 182 may be staggered such that the lower anchor portion 182 is initially directed into the commissure 14 and through the native mitral valve 16. As shown, the upper and lower helical anchor portions 180, 182 wind or rotate in opposite directions and then may be crimped together, as shown or may be precrimped or otherwise attached prior to loading the catheter 10.

Figure 22A:
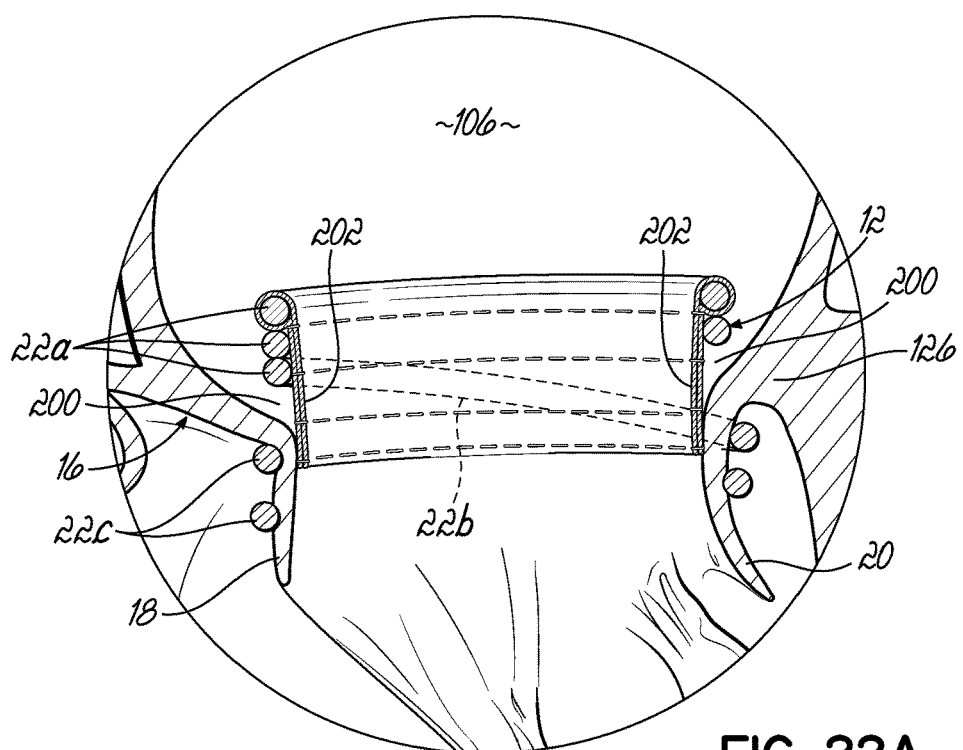
FIG. 22A is a cross-sectional view showing another illustrative embodiment of a helical anchor including a seal.
Figure 22B:
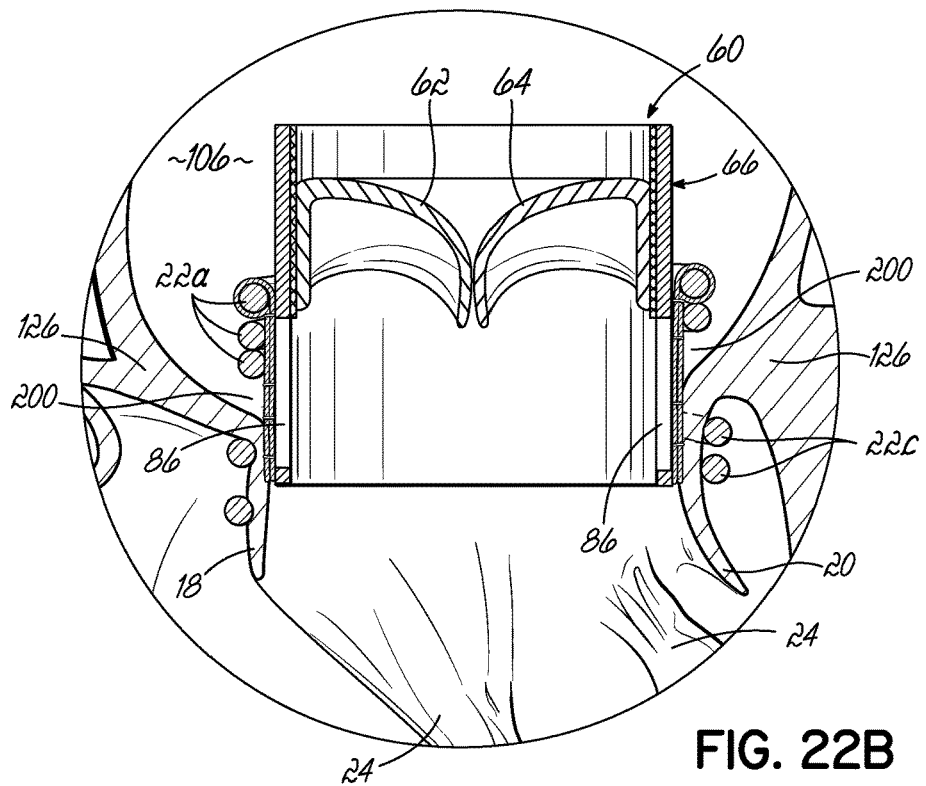
FIG. 22B is a cross-sectional view similar to FIG. 22A, but showing the helical anchor implanted at the location of a native mitral valve and an expandable stent mounted replacement valve held within the helical anchor.

FIGS. 22A and 22B illustrate another embodiment of a helical anchor and replacement valve system similar to those discussed in connection with the above-incorporated PCT Application Serial No. PCT/US2014/050525. In this embodiment, however, the configuration of the helical anchor 12 is shown to have a gap 200 between at least the upper coils 22a and the native mitral valve 16. As in the above incorporated PCT application, the helical anchor 12 includes an annular seal 202 of any desired configuration extending lengthwise through or otherwise along the length of the anchor 12. In this embodiment, a panel or membrane seal 202 is shown extending downwardly from one of the coils 22a and covering the portion of the stent mounted replacement valve 60 that would otherwise be open due to the stent structure 86. The seal 202 therefore prevents leakage of blood past the replacement valve 60 through the open stent structure 86. All other aspects of the assembly as shown in FIGS. 22A and 22B are as described herein and may include any of the options or features described herein or otherwise, for example, in the above-incorporated PCT applications. The gap 200 is formed by a coil portion 22b extending non-parallel to the adjacent coil portions 22a, 22c.

Figure 23A:
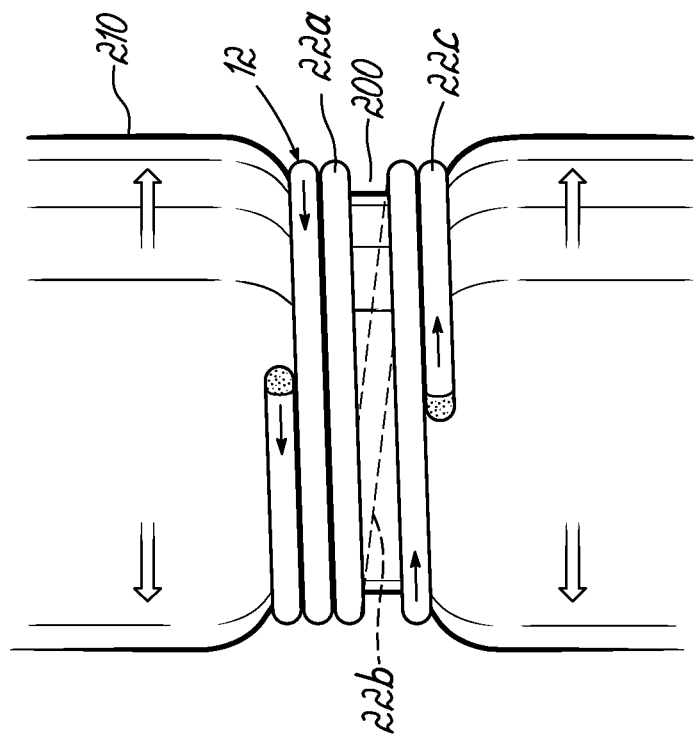
FIG. 23A is a schematic elevational view showing another illustrative embodiment of a helical anchor before expansion with a balloon catheter.
Figure 23B:
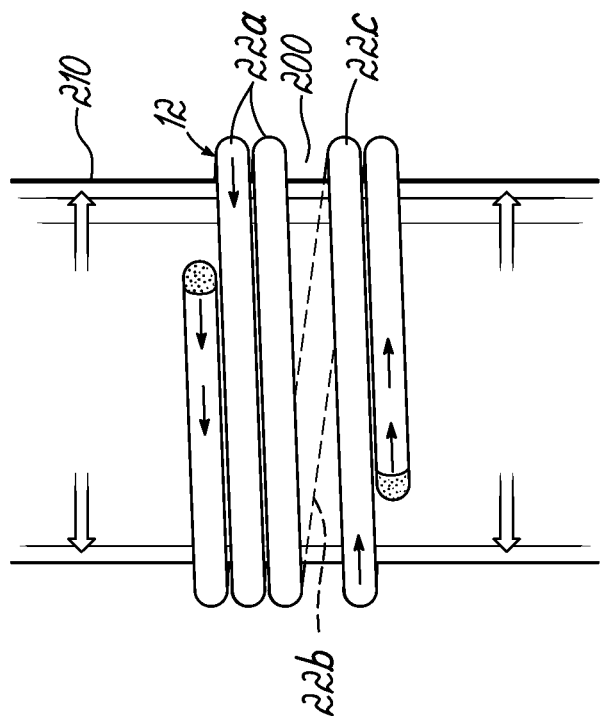
FIG. 23B is an elevational view similar to FIG. 23A, but illustrating the helical anchor during expansion by the balloon catheter.

FIGS. 23A and 23B illustrate another embodiment of a helical anchor 12, again similar to the above-incorporated PCT Application Serial No. PCT/US2014/050525. The difference between this embodiment and the similar embodiment shown in the above-incorporated PCT application is that a gap 200 has been created between two of the middle coils 22a, 22c of the anchor 12. These two figures illustrate the feature of the helical anchor 12 in which the coils 22 will move or rotate as the expandable anchor 12 is expanded by, for example, a balloon catheter 210. As previously described, a gap 200 formed between adjacent coils 22a, 22c may be used to ensure that native mitral tissue is not trapped or engaged by the adjacent coils 22a, 22c. The gap 200 is formed by a coil portion 22b extending non-parallel to the adjacent coil portions 22a, 22c.

While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in any combination depending on the needs and preferences of the operator. This has been a description of the present invention, along with the preferred methods of practicing the present invention as currently known. However, the invention itself should only be defined by the appended claims.

What is claimed is:

1. A system, comprising:
    an expansible prosthetic heart valve comprising a stent structure and leaflets mounted to the stent structure;
    an anchor comprising at least three coils configured to support the prosthetic heart valve and to encircle native tissue of a native heart valve;
    wherein the prosthetic heart valve is capable of being delivered into the anchor and expanded inside the at least three coils to trap the native tissue between the anchor and the prosthetic heart valve; and
    a seal structure on the prosthetic heart valve configured to inhibit blood leakage past the prosthetic heart valve after implantation of the prosthetic heart valve in the anchor, wherein the seal structure comprises a seal layer circumscribing the scent structure and a bumper region covering an end edge of an outflow end of the stent structure, the seal structure arranged such that the entire end edge of the outflow end of the stent structure is covered.

2. The system of claim 1, wherein a first coil of the at least three coils has a first diameter in an unstressed state that is expandable to a second, larger diameter as the prosthetic heart valve, and wherein a second coil of the at least three coils moves from a larger diameter to a smaller diameter as the prosthetic heart valve is expanded inside the multiple coils.

3. The system of claim 1, wherein the seal includes portions extending between adjacent coils for preventing blood leakage through the anchor and past the prosthetic heart valve.

4. The system of claim 1, wherein the seal comprises a biological material.

5. The system of claim 1, wherein at least a portion of the stent structure extends into an interior of the bumper region.

6. The system of claim 1, wherein the seal comprises at least two different materials.

7. The system of claim 6, wherein one of the at least two different materials is pericardium tissue.

8. The system of claim 6, wherein one of the at least two different materials is a foam material.

9. The system of claim 1, wherein the bumper region comprises a first material covering the end edge of the outflow end and a second material covering the first material.

10. The system of claim 1, wherein a gap is formed between two adjacent coil portions of the anchor by a portion of the anchor that extends non-parallel to the adjacent coil portions of the anchor.

11. The system of claim 1, wherein the stent structure is an open stent structure and the seal is configured to, cover openings in the open stent structure.

12. A system, comprising:
a prosthetic heart valve comprising a stent structure and a valve structure mounted to the stent structure, wherein the prosthetic heart valve is expandable from a compressed configuration to an expanded configuration;
an anchor comprising multiple coils configured to be implanted at a native heart valve and adapted to support the prosthetic heart valve, wherein the anchor is configured such that application of a radial outward force, by the prosthetic heart valve expanding from the compressed configuration to the expanded configuration within the anchor, can cause at least one coil of the multiple coils to expand from a first diameter to a second, larger diameter; and
a seal structure on the prosthetic heart valve, wherein the seal structure comprises a seal layer circumscribing the stent structure and a bumper covering the outflow end of the stent structure, the seal structure arranged such that the entire outflow end of the stent structure is covered by the seal structure; and
wherein the prosthetic heart valve and the anchor are configured such that, when the anchor is implanted at the native heart valve, the prosthetic heart valve can be delivered inside the multiple coils of the anchor and expanded such that native tissue of the native heart valve is trapped between the at least one coil and the prosthetic heart valve.

13. The system of claim 12, wherein the anchor includes a coil configured to transition from a larger diameter to a smaller diameter as the prosthetic heart valve is expanded inside the multiple coils.

14. The system of claim 12, wherein the outflow end is flared radially outward.

15. The system of claim 12, wherein a gap is formed between two adjacent coil portions by a region of the anchor that extends non-parallel to the adjacent coil portions of the anchor.

16. The system of claim 12, wherein the multiple coils comprise at least three full coils.

17. The system of claim 12, wherein at least a portion of the stent structure extends into a center of the bumper.

18. The system of claim 12, wherein the seal comprises at least two different materials.

19. The system of claim 18, wherein one of the at least two different materials is pericardium tissue.

20. The system of claim 12, wherein the bumper comprises a first material covering an end edge of the outflow end and a second material covering the first material.

21. The system of claim 12, wherein the stent structure is an open stent structure and the seal structure is configured to cover openings in the open stent structure.

22. The system of claim 12, wherein the anchor comprises a layer of foam material over a wire portion.

23. The system of claim 12, wherein the anchor comprises an upper anchor portion and a lower anchor portion that wind in opposite directions and are crimped together.

* * * * *